(12) United States Patent
Degtiar et al.

(10) Patent No.: US 10,420,880 B2
(45) Date of Patent: Sep. 24, 2019

(54) KEY FOR SECURING COMPONENTS OF A DRUG DELIVERY SYSTEM DURING ASSEMBLY AND/OR TRANSPORT AND METHODS OF USING SAME

(71) Applicant: MEDIMOP Medical Projects Ltd., Ra'anana (IL)

(72) Inventors: Boris Degtiar, Modiin (IL); Yossi Bar-El, Beit Arye (IL); Reuven Y. Filman, Netanya (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 951 days.

(21) Appl. No.: 13/874,121

(22) Filed: Apr. 30, 2013

(65) Prior Publication Data

US 2013/0296799 A1 Nov. 7, 2013

Related U.S. Application Data

(63) Continuation-in-part of application No. 12/244,666, filed on Oct. 2, 2008, now Pat. No. 9,173,997.

(Continued)

(51) Int. Cl.
*A61M 5/14* (2006.01)
*A61M 5/142* (2006.01)
(Continued)

(52) U.S. Cl.
CPC ...... *A61M 5/14248* (2013.01); *A61M 5/1452* (2013.01); *A61M 5/14566* (2013.01);
(Continued)

(58) Field of Classification Search
CPC .......... A61M 5/14566; A61M 5/14248; A61M 5/1452
See application file for complete search history.

(56) References Cited

U.S. PATENT DOCUMENTS

| 232,432 A | 9/1880 | Allison |
|---|---|---|
| 1,795,630 A | 3/1931 | Wilson |

(Continued)

FOREIGN PATENT DOCUMENTS

| CN | 1505535 A | 6/2004 |
|---|---|---|
| CN | 1747683 A | 3/2006 |

(Continued)

OTHER PUBLICATIONS

Office Action dated Sep. 9, 2015 in U.S. Appl. No. 13/643,470 by Alon.

(Continued)

*Primary Examiner* — Bhisma Mehta
*Assistant Examiner* — Matthew A Engel
(74) *Attorney, Agent, or Firm* — Panitch Schwarze Belisario & Nadel LLP

(57) ABSTRACT

A method of securing an assembly of a drug delivery system, comprising: configuring at least a first component and a second component of the assembly in a closed configuration ready for placement into the drug delivery system; installing an assembly key including a locking element on the assembly to secure the assembly in said configuration; and, transporting the assembly with the assembly key installed.

24 Claims, 13 Drawing Sheets

Related U.S. Application Data

(60) Provisional application No. 60/997,459, filed on Oct. 2, 2007.

(51) Int. Cl.
  *A61M 5/145* (2006.01)
  *A61M 5/168* (2006.01)
  *A61M 5/172* (2006.01)
  *A61M 5/315* (2006.01)

(52) U.S. Cl.
  CPC ....... *A61M 5/31501* (2013.01); *A61M 5/1413* (2013.01); *A61M 5/16827* (2013.01); *A61M 5/1723* (2013.01); *A61M 2005/1426* (2013.01); *A61M 2005/14252* (2013.01); *A61M 2005/14268* (2013.01); *A61M 2005/31518* (2013.01); *A61M 2205/3523* (2013.01); *A61M 2205/3569* (2013.01); *A61M 2207/10* (2013.01)

(56) References Cited

U.S. PATENT DOCUMENTS

| | | |
|---|---|---|
| 2,453,590 A | 11/1948 | Poux |
| 2,677,373 A | 5/1954 | Barradas |
| 2,702,547 A | 2/1955 | Glass |
| 2,860,635 A | 11/1958 | Wilburn |
| 3,203,269 A * | 8/1965 | Perrine .................. B64C 13/00 74/89.35 |
| 3,212,685 A * | 10/1965 | Swan ...................... A61M 3/00 222/386 |
| 3,623,474 A | 11/1971 | Heilman et al. |
| 3,708,945 A | 1/1973 | Klettke |
| 3,794,028 A | 2/1974 | Mueller et al. |
| 3,994,295 A | 11/1976 | Wulff |
| 4,189,065 A | 2/1980 | Herold |
| 4,195,636 A | 4/1980 | Behnke |
| 4,218,724 A | 8/1980 | Kaufman |
| 4,254,768 A | 3/1981 | Ty |
| 4,273,122 A | 6/1981 | Whitney et al. |
| 4,300,554 A | 11/1981 | Hessberg et al. |
| 4,324,262 A | 4/1982 | Hall |
| 4,403,987 A | 9/1983 | Gottinger |
| 4,425,120 A | 1/1984 | Sampson et al. |
| 4,435,173 A | 3/1984 | Siposs et al. |
| 4,465,478 A | 8/1984 | Sabelman et al. |
| 4,502,488 A | 3/1985 | Degironimo et al. |
| 4,504,263 A | 3/1985 | Steuer et al. |
| 4,549,554 A | 10/1985 | Markham |
| 4,564,054 A | 1/1986 | Gustavsson |
| 4,565,543 A | 1/1986 | Bekkering et al. |
| 4,583,974 A | 4/1986 | Kokernak |
| 4,585,439 A | 4/1986 | Michel |
| 4,599,082 A | 7/1986 | Grimard |
| 4,601,702 A | 7/1986 | Hudson |
| 4,664,654 A | 5/1987 | Strauss |
| 4,685,903 A | 8/1987 | Cable et al. |
| 4,695,274 A | 9/1987 | Fox |
| 4,698,055 A | 10/1987 | Sealfon |
| 4,702,738 A | 10/1987 | Spencer |
| 4,735,311 A | 4/1988 | Lowe et al. |
| 4,737,144 A | 4/1988 | Choksi |
| 4,772,272 A | 9/1988 | McFarland |
| 4,810,215 A | 3/1989 | Kaneko |
| 4,810,249 A | 3/1989 | Haber et al. |
| 4,813,426 A | 3/1989 | Haber et al. |
| 4,840,185 A | 6/1989 | Hernandez |
| 4,850,966 A | 7/1989 | Grau et al. |
| 4,867,743 A | 9/1989 | Vaillancourt |
| 4,874,383 A | 10/1989 | McNaughton |
| 4,882,575 A | 11/1989 | Kawahara |
| 4,886,499 A | 12/1989 | Cirelli et al. |
| 4,892,521 A | 1/1990 | Laico et al. |
| 4,897,083 A | 1/1990 | Martell |
| 4,900,310 A | 2/1990 | Ogle, II |
| 4,915,702 A | 4/1990 | Haber |
| 4,919,596 A | 4/1990 | Slate et al. |
| 4,923,446 A | 5/1990 | Page et al. |
| 4,929,241 A | 5/1990 | Kulli |
| 4,950,241 A | 8/1990 | Ranford |
| 4,950,246 A | 8/1990 | Muller |
| 4,964,866 A | 10/1990 | Szwarc |
| 4,994,045 A | 2/1991 | Ranford |
| 4,998,924 A | 3/1991 | Ranford |
| 5,019,051 A | 5/1991 | Hake |
| 5,051,109 A | 9/1991 | Simon |
| D322,671 S | 12/1991 | Szwarc |
| 5,088,988 A | 2/1992 | Talonn et al. |
| 5,109,850 A | 5/1992 | Blanco et al. |
| 5,112,317 A | 5/1992 | Michel |
| 5,127,910 A | 7/1992 | Talonn et al. |
| 5,131,816 A | 7/1992 | Brown et al. |
| 5,147,326 A | 9/1992 | Talonn et al. |
| 5,156,599 A | 10/1992 | Ranford et al. |
| 5,190,521 A | 3/1993 | Hubbard et al. |
| 5,217,437 A | 6/1993 | Talonn et al. |
| 5,254,096 A | 10/1993 | Rondelet et al. |
| 5,267,977 A | 12/1993 | Feeney, Jr. |
| 5,269,762 A | 12/1993 | Armbruster et al. |
| 5,300,045 A | 4/1994 | Plassche, Jr. |
| 5,318,522 A | 6/1994 | D'Antonio |
| 5,338,311 A | 8/1994 | Mahurkar |
| 5,342,313 A | 8/1994 | Campbell et al. |
| 5,348,544 A | 9/1994 | Sweeney et al. |
| 5,366,498 A | 11/1994 | Brannan et al. |
| 5,383,865 A * | 1/1995 | Michel .............. A61M 5/31553 604/186 |
| 5,415,645 A | 5/1995 | Friend et al. |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,624 A | 10/1996 | Righi et al. |
| 5,562,686 A | 10/1996 | Sauer et al. |
| 5,593,390 A | 1/1997 | Castellano et al. |
| 5,609,580 A | 3/1997 | Kwiatkowski et al. |
| 5,611,785 A | 3/1997 | Mito et al. |
| 5,616,132 A | 4/1997 | Newman |
| 5,624,400 A | 4/1997 | Firth et al. |
| 5,637,095 A | 6/1997 | Nason et al. |
| 5,643,218 A | 7/1997 | Lynn et al. |
| 5,645,530 A | 7/1997 | Boukhny et al. |
| 5,645,955 A | 7/1997 | Maglica |
| 5,647,853 A | 7/1997 | Feldmann et al. |
| 5,658,256 A | 8/1997 | Shields |
| 5,662,678 A | 9/1997 | Macklin |
| 5,672,160 A | 9/1997 | Osterlind et al. |
| 5,690,618 A | 11/1997 | Smith et al. |
| 5,697,908 A | 12/1997 | Imbert et al. |
| 5,728,075 A * | 3/1998 | Levander ............ A61M 5/2448 604/211 |
| D393,314 S | 4/1998 | Meisner et al. |
| 5,741,275 A * | 4/1998 | Wyssmann ....... A61M 5/14526 604/143 |
| 5,766,186 A | 6/1998 | Faraz et al. |
| 5,795,675 A | 8/1998 | Maglica |
| 5,800,420 A | 9/1998 | Gross et al. |
| 5,807,375 A | 9/1998 | Gross et al. |
| 5,810,784 A | 9/1998 | Tamaro |
| 5,814,020 A | 9/1998 | Gross |
| 5,830,187 A | 11/1998 | Kriesel et al. |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,893,842 A | 4/1999 | Imbert |
| 5,894,015 A | 4/1999 | Rechtin |
| 5,919,167 A | 7/1999 | Mulhauser et al. |
| 5,926,596 A * | 7/1999 | Edwards ............. G02B 6/3834 385/78 |

(56) References Cited

U.S. PATENT DOCUMENTS

| | | | |
|---|---|---|---|
| 5,931,814 | A | 8/1999 | Alex et al. |
| 5,941,850 | A | 8/1999 | Shah et al. |
| 5,944,699 | A | 8/1999 | Barrelle et al. |
| 5,948,392 | A | 9/1999 | Haslwanter et al. |
| 5,954,697 | A | 9/1999 | Srisathapat et al. |
| 5,957,895 | A | 9/1999 | Sage et al. |
| 5,968,011 | A | 10/1999 | Larsen et al. |
| 5,989,221 | A | 11/1999 | Hjertman |
| 5,993,423 | A * | 11/1999 | Choi ............... A61M 5/158 128/DIG. 12 |
| 6,004,296 | A | 12/1999 | Jansen et al. |
| 6,004,297 | A | 12/1999 | Steenfeldt-Jensen et al. |
| 6,033,245 | A | 3/2000 | Yamkovoy |
| 6,033,377 | A | 3/2000 | Rasmussen et al. |
| 6,045,533 | A | 4/2000 | Kriesel et al. |
| 6,064,797 | A | 5/2000 | Crittendon et al. |
| 6,074,369 | A | 6/2000 | Sage et al. |
| 6,162,197 | A | 12/2000 | Mohammad |
| 6,186,982 | B1 | 2/2001 | Gross et al. |
| 6,200,289 | B1 | 3/2001 | Hochman et al. |
| 6,200,296 | B1 | 3/2001 | Dibiasi et al. |
| 6,224,569 | B1 | 5/2001 | Brimhall |
| 6,248,093 | B1 * | 6/2001 | Moberg ............. A61M 5/1456 128/DIG. 12 |
| 6,270,481 | B1 | 8/2001 | Mason et al. |
| 6,277,095 | B1 | 8/2001 | Kriesel et al. |
| 6,277,098 | B1 | 8/2001 | Klitmose et al. |
| 6,277,099 | B1 * | 8/2001 | Strowe ............. A61M 5/31553 604/186 |
| 6,287,283 | B1 | 9/2001 | Ljunggreen et al. |
| 6,293,925 | B1 | 9/2001 | Safabash et al. |
| 6,302,633 | B1 | 10/2001 | Poe |
| 6,336,729 | B1 | 1/2002 | Pavelle et al. |
| 6,345,968 | B1 | 2/2002 | Shupe |
| 6,377,848 | B1 | 4/2002 | Garde et al. |
| 6,391,005 | B1 | 5/2002 | Lum et al. |
| 6,423,029 | B1 | 7/2002 | Elsberry |
| D465,026 | S | 10/2002 | May et al. |
| 6,458,102 | B1 | 10/2002 | Mann et al. |
| 6,485,461 | B1 | 11/2002 | Mason et al. |
| 6,485,465 | B2 * | 11/2002 | Moberg ............. A61M 5/1456 417/18 |
| 6,500,150 | B1 | 12/2002 | Gross et al. |
| 6,503,231 | B1 | 1/2003 | Prausnitz et al. |
| 6,511,336 | B1 | 1/2003 | Turek et al. |
| 6,517,517 | B1 | 2/2003 | Farrugia et al. |
| D471,274 | S | 3/2003 | Diaz et al. |
| D471,983 | S | 3/2003 | Hippolyte et al. |
| 6,554,800 | B1 | 4/2003 | Nezhadian et al. |
| 6,558,351 | B1 | 5/2003 | Steil et al. |
| 6,565,541 | B2 | 5/2003 | Sharp |
| 6,589,229 | B1 | 7/2003 | Connelly et al. |
| 6,595,956 | B1 | 7/2003 | Gross et al. |
| 6,595,960 | B2 | 7/2003 | West et al. |
| 6,645,181 | B1 | 11/2003 | Lavi et al. |
| 6,652,482 | B2 | 11/2003 | Hochman |
| 6,656,158 | B2 | 12/2003 | Mahoney et al. |
| 6,656,159 | B2 | 12/2003 | Flaherty |
| 6,659,980 | B2 | 12/2003 | Moberg et al. |
| 6,673,033 | B1 | 1/2004 | Sciulli et al. |
| 6,679,862 | B2 | 1/2004 | Diaz et al. |
| 6,689,118 | B2 | 2/2004 | Alchas et al. |
| 6,699,218 | B2 | 3/2004 | Flaherty et al. |
| 6,722,916 | B2 | 4/2004 | Buccinna et al. |
| 6,743,211 | B1 | 6/2004 | Prausnitz et al. |
| 6,749,587 | B2 | 6/2004 | Flaherty |
| 6,752,783 | B2 | 6/2004 | Hung et al. |
| 6,752,787 | B1 | 6/2004 | Causey, III et al. |
| 6,768,425 | B2 | 7/2004 | Flaherty et al. |
| 6,786,890 | B2 * | 9/2004 | Preuthun ........... A61M 5/14566 604/155 |
| 6,800,071 | B1 | 10/2004 | McConnell et al. |
| 6,805,687 | B2 | 10/2004 | Dextradeur et al. |
| 6,824,529 | B2 | 11/2004 | Gross et al. |
| 6,843,782 | B2 | 1/2005 | Gross et al. |
| 6,854,620 | B2 | 2/2005 | Ramey |
| 6,905,298 | B1 | 6/2005 | Haring |
| 6,908,452 | B2 | 6/2005 | Diaz et al. |
| 6,960,192 | B1 | 11/2005 | Flaherty et al. |
| 6,997,727 | B1 | 2/2006 | Legrady et al. |
| 7,001,360 | B2 | 2/2006 | Veasey et al. |
| 7,033,338 | B2 | 4/2006 | Vilks et al. |
| 7,034,223 | B2 | 4/2006 | Fan et al. |
| 7,048,715 | B2 | 5/2006 | Diaz et al. |
| 7,060,054 | B2 | 6/2006 | Nissels |
| 7,060,059 | B2 | 6/2006 | Keith et al. |
| 7,066,909 | B1 | 6/2006 | Peter et al. |
| 7,097,637 | B2 | 8/2006 | Triplett et al. |
| 7,128,727 | B2 | 10/2006 | Flaherty et al. |
| 7,144,384 | B2 | 12/2006 | Gorman et al. |
| D544,092 | S | 6/2007 | Lewis |
| 7,225,694 | B2 * | 6/2007 | Said ............. F16H 25/20 74/89.35 |
| 7,247,149 | B2 | 7/2007 | Beyerlein |
| 7,250,037 | B2 | 7/2007 | Shermer et al. |
| 7,267,669 | B2 | 9/2007 | Staunton et al. |
| 7,291,132 | B2 | 11/2007 | DeRuntz et al. |
| 7,291,159 | B2 | 11/2007 | Schmelzeisen-Redeker et al. |
| 7,303,549 | B2 | 12/2007 | Flaherty et al. |
| 7,344,385 | B2 | 3/2008 | Chen |
| 7,364,570 | B2 | 4/2008 | Gerondale et al. |
| 7,390,312 | B2 | 6/2008 | Barrelle |
| 7,390,314 | B2 | 6/2008 | Stutz, Jr. et al. |
| 7,407,493 | B2 | 8/2008 | Cane' |
| D578,210 | S | 10/2008 | Muta et al. |
| 7,442,186 | B2 | 10/2008 | Blomquist |
| 7,455,663 | B2 | 11/2008 | Bikovsky |
| 7,465,290 | B2 | 12/2008 | Reilly |
| 7,488,181 | B2 | 2/2009 | van Haaster |
| 7,497,842 | B2 | 3/2009 | Diaz et al. |
| 7,501,587 | B2 | 3/2009 | English |
| 7,503,786 | B2 | 3/2009 | Kato et al. |
| 7,530,964 | B2 | 5/2009 | Lavi et al. |
| 7,540,858 | B2 | 6/2009 | DiBiasi |
| 7,547,281 | B2 | 6/2009 | Hayes et al. |
| 7,565,208 | B2 | 7/2009 | Harris et al. |
| 7,569,050 | B2 | 8/2009 | Moberg et al. |
| D600,341 | S | 9/2009 | Loerwald |
| 7,585,287 | B2 | 9/2009 | Bresina et al. |
| 7,588,559 | B2 | 9/2009 | Aravena et al. |
| 7,589,974 | B2 | 9/2009 | Grady et al. |
| D602,155 | S | 10/2009 | Foley et al. |
| D602,586 | S | 10/2009 | Foley et al. |
| D604,835 | S | 11/2009 | Conley |
| 7,628,770 | B2 | 12/2009 | Ethelfeld |
| 7,628,772 | B2 | 12/2009 | McConnell et al. |
| 7,628,782 | B2 | 12/2009 | Adair et al. |
| 7,637,891 | B2 | 12/2009 | Wall |
| 7,637,899 | B2 | 12/2009 | Woolston et al. |
| 7,641,649 | B2 | 1/2010 | Moberg et al. |
| 7,660,627 | B2 | 2/2010 | McNichols et al. |
| 7,678,079 | B2 | 3/2010 | Shermer et al. |
| 7,682,338 | B2 | 3/2010 | Griffin |
| 7,686,787 | B2 | 3/2010 | Moberg et al. |
| 7,699,829 | B2 | 4/2010 | Harris et al. |
| 7,699,833 | B2 | 4/2010 | Moberg et al. |
| 7,704,088 | B2 | 4/2010 | Sakamoto |
| 7,704,227 | B2 | 4/2010 | Moberg et al. |
| 7,704,229 | B2 | 4/2010 | Moberg et al. |
| 7,704,231 | B2 | 4/2010 | Pongpairochana et al. |
| 7,708,717 | B2 | 5/2010 | Estes et al. |
| 7,713,238 | B2 | 5/2010 | Mernoe |
| 7,713,240 | B2 | 5/2010 | Istoc et al. |
| 7,717,903 | B2 | 5/2010 | Estes et al. |
| 7,717,913 | B2 | 5/2010 | Novak et al. |
| 7,722,574 | B2 | 5/2010 | Toman et al. |
| 7,736,344 | B2 | 6/2010 | Moberg et al. |
| 7,744,589 | B2 | 6/2010 | Mounce et al. |
| 7,749,194 | B2 | 7/2010 | Edwards et al. |
| 7,766,867 | B2 | 8/2010 | Lynch et al. |
| 7,776,030 | B2 | 8/2010 | Estes et al. |
| 7,780,637 | B2 | 8/2010 | Jerde et al. |
| 7,789,857 | B2 | 9/2010 | Moberg et al. |

(56) References Cited

U.S. PATENT DOCUMENTS

| | | |
|---|---|---|
| 7,794,426 B2 | 9/2010 | Briones et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 * | 6/2011 | Cabiri .............. A61M 5/14566 604/154 |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,177,749 B2 | 5/2012 | Slate et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,348,898 B2 | 1/2013 | Cabiri |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,425,468 B2 | 4/2013 | Weston |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,512,295 B2 | 8/2013 | Evans et al. |
| 8,517,987 B2 | 8/2013 | Istoc et al. |
| 8,523,803 B1 | 9/2013 | Favreau |
| 8,551,046 B2 | 10/2013 | Causey et al. |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,622,966 B2 | 1/2014 | Causey et al. |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,920,374 B2 | 12/2014 | Bokelman et al. |
| 8,979,802 B2 | 3/2015 | Woehr |
| 9,011,164 B2 | 4/2015 | Filman et al. |
| 9,061,104 B2 | 6/2015 | Daniel |
| 9,061,110 B2 | 6/2015 | Avery et al. |
| 9,072,827 B2 | 7/2015 | Cabiri |
| 9,089,475 B2 | 7/2015 | Fangrow |
| 9,089,641 B2 | 7/2015 | Kavazov |
| 9,149,575 B2 | 10/2015 | Cabiri |
| 9,173,997 B2 * | 11/2015 | Gross .............. A61M 5/14566 |
| D747,799 S | 1/2016 | Norton et al. |
| 9,314,569 B2 | 4/2016 | Causey et al. |
| 9,350,634 B2 | 5/2016 | Fadell |
| 9,393,365 B2 | 7/2016 | Cabiri |
| 9,421,323 B2 | 8/2016 | Cabiri et al. |
| 9,452,261 B2 | 9/2016 | Alon |
| 9,522,234 B2 | 12/2016 | Cabiri |
| 9,539,388 B2 | 1/2017 | Causey et al. |
| 9,572,926 B2 | 2/2017 | Cabiri |
| 9,656,019 B2 | 5/2017 | Cabiri et al. |
| 9,782,545 B2 * | 10/2017 | Gross .............. A61M 5/14566 |
| 2001/0005781 A1 | 6/2001 | Bergens et al. |
| 2001/0018937 A1 | 9/2001 | Nemoto |
| 2001/0025168 A1 | 9/2001 | Gross et al. |
| 2001/0034502 A1 | 10/2001 | Moberg et al. |
| 2001/0041869 A1 | 11/2001 | Causey et al. |
| 2002/0010423 A1 | 1/2002 | Gross et al. |
| 2002/0016569 A1 | 2/2002 | Critchlow et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2003/0009133 A1 * | 1/2003 | Ramey .............. A61M 5/1456 604/155 |
| 2003/0014018 A1 * | 1/2003 | Giambattista ........ A61M 5/002 604/198 |
| 2003/0069518 A1 | 4/2003 | Daley et al. |

(56) References Cited

U.S. PATENT DOCUMENTS

| | | |
|---|---|---|
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0167039 A1 | 9/2003 | Moberg |
| 2003/0171717 A1 | 9/2003 | Farrugia et al. |
| 2003/0216683 A1 | 11/2003 | Shekalim |
| 2004/0000818 A1 | 1/2004 | Preuthun et al. |
| 2004/0010207 A1 | 1/2004 | Flaherty et al. |
| 2004/0049160 A1 | 3/2004 | Hsieh et al. |
| 2004/0049161 A1 | 3/2004 | Shearn |
| 2004/0082911 A1 | 4/2004 | Tiu et al. |
| 2004/0092873 A1* | 5/2004 | Moberg .............. A61M 5/1456 604/131 |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0186441 A1 | 9/2004 | Graf et al. |
| 2004/0210196 A1 | 10/2004 | Bush, Jr. et al. |
| 2004/0260233 A1 | 12/2004 | Garibotto et al. |
| 2005/0033234 A1 | 2/2005 | Sadowski et al. |
| 2005/0038391 A1 | 2/2005 | Wittland et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | Dilanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0036216 A1 | 2/2006 | Rimlinger et al. |
| 2006/0095010 A1 | 5/2006 | Westbye |
| 2006/0095014 A1 | 5/2006 | Ethelfeld |
| 2006/0122577 A1 | 6/2006 | Poulsen et al. |
| 2006/0124269 A1 | 6/2006 | Miyazaki et al. |
| 2006/0173406 A1 | 8/2006 | Hayes et al. |
| 2006/0173439 A1 | 8/2006 | Thorne et al. |
| 2006/0184154 A1 | 8/2006 | Moberg et al. |
| 2006/0195029 A1 | 8/2006 | Shults et al. |
| 2006/0206054 A1 | 9/2006 | Shekalim |
| 2006/0211982 A1 | 9/2006 | Prestrelski et al. |
| 2006/0229569 A1* | 10/2006 | Lavi ...................... A61M 5/326 604/197 |
| 2006/0264888 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0025879 A1 | 2/2007 | Vandergaw |
| 2007/0049865 A1 | 3/2007 | Radmer et al. |
| 2007/0073228 A1 | 3/2007 | Mernoe et al. |
| 2007/0118405 A1 | 5/2007 | Campbell et al. |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097326 A1 | 4/2008 | Moberg et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215013 A1 | 9/2008 | Felix-Faure |
| 2008/0215015 A1 | 9/2008 | Cindrich et al. |
| 2008/0243087 A1* | 10/2008 | Enggaard .......... A61M 5/31553 604/208 |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319383 A1 | 12/2008 | Byland et al. |
| 2008/0319416 A1 | 12/2008 | Yodfat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076383 A1 | 3/2009 | Toews et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093763 A1 | 4/2009 | Gonnelli et al. |
| 2009/0093792 A1* | 4/2009 | Gross ................ A61M 5/14566 604/518 |
| 2009/0093793 A1 | 4/2009 | Gross et al. |
| 2009/0105650 A1* | 4/2009 | Wiegel .............. A61M 5/14244 604/152 |
| 2009/0105663 A1 | 4/2009 | Brand et al. |
| 2009/0124977 A1 | 5/2009 | Jensen |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1* | 12/2009 | Shipway .......... A61M 5/14566 604/155 |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0162548 A1 | 7/2010 | Leidig |
| 2010/0168607 A1 | 7/2010 | Miesel |
| 2010/0168683 A1 | 7/2010 | Cabiri |

(56) References Cited

U.S. PATENT DOCUMENTS

| | | |
|---|---|---|
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0092915 A1 | 4/2011 | Olson et al. |
| 2011/0112504 A1 | 5/2011 | Causey et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178472 A1 | 7/2011 | Cabiri |
| 2011/0201998 A1 | 8/2011 | Pongpairochana et al. |
| 2011/0224616 A1 | 9/2011 | Slate et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022496 A1 | 1/2012 | Causey et al. |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041387 A1 | 2/2012 | Bruggemann et al. |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1 | 7/2012 | Bruggemann et al. |
| 2012/0184917 A1 | 7/2012 | Born et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0190693 A1 | 7/2013 | Ekman et al. |
| 2013/0237953 A1 | 9/2013 | Kow et al. |
| 2013/0245595 A1 | 9/2013 | Kow et al. |
| 2013/0245596 A1* | 9/2013 | Cabiri ............... A61M 5/1413 604/500 |
| 2013/0253419 A1 | 9/2013 | Favreau |
| 2013/0253420 A1 | 9/2013 | Favreau |
| 2013/0253421 A1 | 9/2013 | Favreau |
| 2013/0267895 A1 | 10/2013 | Hemmingsen |
| 2013/0296799 A1 | 11/2013 | Degtiar et al. |
| 2013/0304021 A1 | 11/2013 | Cabiri et al. |
| 2013/0310753 A1 | 11/2013 | Cabiri |
| 2013/0323699 A1 | 12/2013 | Edwards et al. |
| 2013/0331791 A1 | 12/2013 | Gross et al. |
| 2013/0338584 A1 | 12/2013 | Mounce et al. |
| 2014/0018735 A1 | 1/2014 | Causey et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0121633 A1 | 5/2014 | Causey et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |
| 2016/0228652 A1 | 8/2016 | Cabiri et al. |
| 2016/0296716 A1 | 10/2016 | Cabiri et al. |
| 2016/0346478 A1 | 12/2016 | Bar-El et al. |
| 2019/0022306 A1 | 1/2019 | Gibson et al. |

FOREIGN PATENT DOCUMENTS

| | | |
|---|---|---|
| CN | 1863566 A | 11/2006 |
| CN | 101090749 A | 12/2007 |
| CN | 101227943 A | 7/2008 |
| CN | 101448536 A | 6/2009 |
| CN | 101522235 A | 9/2009 |
| CN | 101541362 A | 9/2009 |
| CN | 201692438 U | 1/2011 |
| CN | 201941304 U | 8/2011 |
| CN | 102186733 A | 9/2011 |
| CN | 102378638 A | 3/2012 |
| DE | 1064693 B | 9/1959 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 1003581 B1 | 11/2000 |
| EP | 1219312 A2 | 7/2002 |
| EP | 1530979 A1 | 5/2005 |
| EP | 1666080 A1 | 6/2006 |
| EP | 2060606 A1 | 5/2009 |
| EP | 2498589 A1 | 9/2012 |
| FR | 2770136 A1 | 4/1999 |
| JP | H07-194701 A | 8/1995 |
| JP | H09-505758 A | 6/1997 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2002528676 A | 9/2002 |
| JP | 2003-501157 A | 1/2003 |
| JP | 2003-527138 A | 9/2003 |
| JP | 2003-534061 A | 11/2003 |
| JP | 2004-501721 A | 1/2004 |
| JP | 2004-512100 A | 4/2004 |
| JP | 2005-523127 A | 8/2005 |
| JP | 2005-270629 A | 10/2005 |
| JP | 2007-509661 A | 4/2007 |
| JP | 2008-534131 A | 8/2008 |
| JP | 2008-220961 A | 9/2008 |
| JP | 2009-502273 A | 1/2009 |
| WO | 9009202 A1 | 8/1990 |
| WO | 9307922 A1 | 4/1993 |
| WO | 9407553 A1 | 4/1994 |
| WO | 9513838 A1 | 5/1995 |
| WO | 9609083 A1 | 3/1996 |
| WO | 9632975 A1 | 10/1996 |

(56) References Cited

FOREIGN PATENT DOCUMENTS

| | | |
|---|---|---|
| WO | 9700091 A1 | 1/1997 |
| WO | 9710012 A1 | 3/1997 |
| WO | 9733638 A1 | 9/1997 |
| WO | 9857683 A1 | 12/1998 |
| WO | 9929151 A1 | 6/1999 |
| WO | 9959665 A1 | 11/1999 |
| WO | 0025844 A1 | 5/2000 |
| WO | 200130421 A2 | 5/2001 |
| WO | 200172357 A2 | 10/2001 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0234315 A1 | 5/2002 |
| WO | 200238204 A2 | 5/2002 |
| WO | 0272182 A1 | 9/2002 |
| WO | 03090833 A1 | 11/2003 |
| WO | 04000397 A1 | 12/2003 |
| WO | 2004032990 A2 | 4/2004 |
| WO | 2004105841 A1 | 12/2004 |
| WO | 2005018703 A2 | 3/2005 |
| WO | 2005037350 A2 | 4/2005 |
| WO | 2005072795 A2 | 8/2005 |
| WO | 2006037434 A1 | 4/2006 |
| WO | 06069380 A1 | 6/2006 |
| WO | 2006102676 A1 | 9/2006 |
| WO | 2006104806 A2 | 10/2006 |
| WO | 2006121921 A2 | 11/2006 |
| WO | 2007017052 A1 | 2/2007 |
| WO | 2007051563 A1 | 5/2007 |
| WO | 2007056504 A1 | 5/2007 |
| WO | 20070073228 A1 | 6/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2009044401 | 4/2009 |
| WO | 2009046989 A2 | 4/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2010089313 A1 | 8/2010 |
| WO | 2011075105 A1 | 6/2011 |
| WO | 2011090955 A1 | 7/2011 |
| WO | 2011090956 A2 | 7/2011 |
| WO | 2011156373 A1 | 12/2011 |
| WO | 2012032411 A2 | 3/2012 |
| WO | 2012040528 A1 | 3/2012 |
| WO | 2012160157 A1 | 11/2012 |
| WO | 2014179774 A1 | 11/2014 |
| WO | 2015114158 A1 | 8/2015 |

OTHER PUBLICATIONS

U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
Office Action dated Sep. 30, 2015 in U.S. Appl. No. 13/667,739 by Cabiri.
Office Action dated Sep. 18, 2015 in U.S. Appl. No. 13/874,085 by Cabiri.
Office Action dated Jul. 31, 2015 in U.S. Appl. No. 13/521,181 by Cabiri.
Office Action dated Aug. 13, 2015 in U.S. Appl. No. 14/553,399 by Cabiri.
Int'l Preliminary Report on Patentability dated Jul. 16, 2015 in Int'l Application No. PCT/US2013/078040.
Notice of Allowance dated Aug. 24, 2015 in U.S. Appl. No. 29/479,307 by Norton.
Extended European Search Report dated Aug. 7, 2014 in EP Application No. 1417477.4.
Office Action dated Aug. 6, 2014 in EP Application No. 11 707 942.6.
Office Action dated Sep. 2, 2014 in JP Application No. 2012-550069.
Office Action dated Sep. 2, 2014 in JP Application No. 2012-550068.
Office Action dated Aug. 26, 2014 in CN Application No. 201180006567.4.
Int'l Preliminary Report on Patentability dated Oct. 9, 2014 in Int'l Application No. PCT/US2013/033118.
Office Action dated Oct. 9, 2014 in U.S. Appl. No. 13/873,335.
Office Action dated Jun. 3, 2014 in JP Application No. 2010-527595.
Office Action dated Jul. 7, 2014 in U.S. Appl. No. 12/244,666 by Gross.
Int'l Search Report and Written Opinion dated Jul. 31, 2014 in Int'l Application No. PCT/US2014/033598.
U.S. Appl. No. 14/258,661 by Cabiri, filed Apr. 22, 2014.
Int'l Search Report and Written Opinion dated Jan. 7, 2014 in Int'l Application No. PCT/US2013/065211.
Office Action dated May 23, 2014 in U.S. Appl. No. 13/472,112 by Cabiri.
U.S. Appl. No. 14/193,692 by Gross, filed Feb. 28, 2014.
Office Action dated Feb. 4, 2014 in EP Application No. 11 707 942.6.
English translation of an Office Action dated Mar. 5, 2014 in CN Application No. 200880117084.X.
Int'l Search Report and Written Opinion dated Apr. 3, 2014 in Int'l Application No. PCT/US2013/078040.
Extended European Search Report dated Mar. 27, 2014 in EP Application No. 14154717.4.
Office Action dated Feb. 28, 2014 in CN Application No. 201180006571.0.
Office Action dated Oct. 9, 2013 in IL Application No. 208634.
Office Action dated Nov. 5, 2013 in JP Application No. 2010-527595.
Office Action dated Sep. 29, 2013 in CN Application No. 201080040968.7.
Office Action dated Nov. 4, 2013 in EP Application No. 11 709 234.6.
Office Action dated Jun. 2, 2016 in CN Application No. 2014101783189.
Office Action dated Dec. 17, 2013 in JP Application No. 2012-529808.
Office Action dated Dec. 10, 2013 in CN Application No. 201180006567.4.
Office Action dated Jan. 8, 2014 in U.S. Appl. No. 13/521,167 by Cabiri.
U.S. Appl. No. 29/479,307 by Norton, filed Jan. 14, 2014.
U.S. Appl. No. 14/593,051 by Gross, filed Jan. 9, 2015.
Int'l Search Report dated May 13, 2009 in Int'l Application No. PCT/IL2008/001312.
Int'l Preliminary Report on Patentability dated Apr. 7, 2010 in Int'l Application No. PCT/IL2008/001312: Written Opinion.
Int'l Search Report dated Apr. 26, 2010 in Int'l Application No. PCT/US2009/069552.
Office Action dated Apr. 5, 2010 in U.S. Appl. No. 12/244,666.
Office Action dated Sep. 21, 2010 in U.S. Appl. No. 12/244,666.
Office Action dated Apr. 5, 2010 in U.S. Appl. No. 12/244,688.
Office Action dated Sep. 2, 2010 in U.S. Appl. No. 12/244,688.
Office Action dated Sep. 30, 2010 in U.S. Appl. No. 12/689,250.
Int'l Search Report dated Jan. 12, 2011 in Int'l Application No. PCT/US2010/048556; Written Opinion.
International Preliminary Report on Patentability dated Jul. 5, 2011 in International Application No. PCT/US2009/069552; Written Opinion.
Office Action dated Jul. 13, 2011 in U.S. Appl. No. 12/559,563.
Int'l Preliminary Report on Patentability dated Sep. 1, 2011 in Int'l Application No. PCT/US2010/048556.
Office Action dated Sep. 6, 2011 in U.S. Appl. No. 12/345,818.
Office Action dated Feb. 21, 2012 in U.S. Appl. No. 12/689,249.
Int'l Search Report dated Jun. 17, 2011 in Int'l Application No. PCT/US2011/021604.

(56) References Cited

OTHER PUBLICATIONS

Int'l Search Report dated Oct. 12, 2011 in Int'l Application No. PCT/US2011/021605.
Office Action dated Oct. 28, 2011 in U.S. Appl. No. 12/615,828.
Int'l Search Report dated Sep. 22, 2011 in Int'l Application No. PCT/IL11/00368; Written Opinion.
U.S. Appl. No. 13/521,181 by Cabiri, filed Jul. 9, 2012.
U.S. Appl. No. 13/521,167 by Cabiri, filed Jul. 9, 2012.
Office Action dated May 16, 2012 in U.S. Appl. No. 12/615,828.
Office Action dated Jul. 2, 2012 in U.S. Appl. No. 13/272,555.
Office Action dated May 3, 2012 in CN Application No. 200880117084.X.
U.S. Appl. No. 13/472,112 by Cabiri, filed May 15, 2012.
U.S. Appl. No. 13/429,840 by Cabiri, filed Mar. 26, 2012.
Int'l Preliminary Report on Patentability dated Aug. 2, 2012 in Int'l Application No. PCT/US2011/021604.
U.S. Appl. No. 13/643,470 by Alon, filed Oct. 25, 2012.
U.S. Appl. No. 13/733,516 by Cabiri, filed Jan. 3, 2013.
Office Action dated Jan. 8, 2013 in JP Application No. 2010-527595.
Int'l Preliminary Report on Patentability dated Feb. 7, 2013 in Int'l Application No. PCT/US2011/021604.
Int'l Preliminary Report on Patentability dated Feb. 7, 2013 in Int'l Application No. PCT/US2011/021605.
English translation of an Office Action dated Jan. 30, 2013 in CN Application No. 200880117084.X.
U.S. Appl. No. 13/873,335 by Filman, filed Apr. 30, 2013.
U.S. Appl. No. 13/892,905 by Cabiri, filed May 13, 2013.
U.S. Appl. No. 13/874,085 by Cabiri, filed Apr. 30, 2013.
U.S. Appl. No. 13/874,017 by Cabiri, filed Apr. 30, 2013.
U.S. Appl. No. 14/683,193 by Cabiri, filed Apr. 10, 2015.
Office Action dated Feb. 20, 2015 in U.S. Appl. No. 13/521,181 by Cabiri.
Office Action dated Feb. 24, 2015 in U.S. Appl. No. 14/258,661 by Cabiri.
U.S. Appl. No. 14/638,525 by Filman, filed Mar. 4, 2015.
Extended European Search Report dated Feb. 23, 2015 in EP Application No. 14166596.8.
Office Action dated Mar. 10, 2015 in U.S. Appl. No. 13/643,470 by Alon.
Office Action dated Mar. 10, 2015 in U.S. Appl. No. 12/244,666 by Gross.
Extended European Search Report dated Feb. 23, 2015 in EP Application No. 14166591.9.
Office Action dated Mar. 10, 2015 in CN Application No. 201180006567.4.
Office Action dated Mar. 31, 2015 in JP Application No. 2012-550068.
Int'l Search Report and Written Opinion dated Jul. 26, 2013 in Int'l Application No. PCT/US2012/039465.
Int'l Search Report and Written Opinion dated Aug. 5, 2013 in Int'l Application No. PCT/US2013/033118.
U.S. Appl. No. 13/964,651 by Gross, filed Aug. 12, 2013.
Office Action dated Aug. 15, 2013 in CN Application No. 200880117084.X.
Int'l Preliminary Report on Patentability dated May 14, 2015 in Int'l Application No. PCT/US2013/065211.
Office Action dated May 7, 2015 in JP Application No. 2012-550069.
Office Action dated May 13, 2015 in CN Application No. 201380025566.3.
U.S. Appl. No. 14/715,791 by Cabiri, filed May 19, 2015.
U.S. Appl. No. 14/725,009 by Bar-El, filed May 29, 2015.
Office Action dated May 1, 2015 in U.S. Appl. No. 14/638,525 by Filman.
Office Action dated Jun. 4, 2015 in U.S. Appl. No. 13/667,739 by Cabiri.
Office Action dated Nov. 5, 2014 in U.S. Appl. No. 13/643,470 by Alon.
U.S. Appl. No. 14/553,399 by Cabiri, filed Nov. 25, 2014.
Office Action dated Nov. 2, 2014 in CN Application No. 201180006571.0.
Office Action dated Nov. 21, 2014 in U.S. Appl. No. 13/472,112 by Cabiri.
Office Action dated Nov. 21, 2014 in U.S. Appl. No. 13/429,840 by Cabiri.
Int'l Preliminary Report on Patentability dated Nov. 27, 2014 in Int'l Application No. PCT/US2013/039465.
Office Action dated May 25, 2016 in U.S. Appl. No. 14/874,017 by Cabiri.
Office Action dated Jun. 10, 2016 in U.S. Appl. No. 13/964,651 by Gross.
Office Action dated May 31, 2016 in U.S. Appl. No. 14/593,051 by Gross.
Office Action dated Apr. 22, 2016 in CN Application No. 2014102892041.
Office Action dated May 5, 2015 in CN Application No. 201180006571.0.
Partial European Search Report dated Nov. 24, 2015 in EP Application No. 14166592.7.
Office Action dated Dec. 1, 2015 in CN Application No. 201410289204.1.
Extended European Search Report dated Mar. 8, 2016 in EP Application No. 14166592.7.
Search Report dated Oct. 14, 2016 in CN Application No. 2014101783742.
Office Action dated Oct. 28, 2016 in CN Application No. 2014101783742.
Office Action dated Jan. 10, 2017 in U.S. Appl. No. 14/193,692, by Gross.
Office Action dated Feb. 16, 2017 in CN Application No. 2014101783189.
Extended European Search Report dated Nov. 10, 2016 in EP Application No. 08808111.2.
Office Action dated Feb. 24, 2017 in U.S. Appl. No. 13/964,651, by Gross.
Office Action dated Nov. 25, 2016 in U.S. Appl. No. 13/874,017, by Cabiri.
Office Action dated Oct. 5, 2016 in U.S. Appl. No. 13/964,651, by Gross.
Office Action dated Dec. 9, 2016 in U.S. Appl. No. 14/593,051, by Gross.
Int'l Search Report and Written Opinion dated Jul. 6, 2017 in Int'l Application No. PCT/US2017/022966.
Office Action dated Jul. 3, 2017 in CN Application No. 2014101783742.
Extended European Search Report dated Jul. 3, 2017 in EP Application No. 16190054.3.
Office Action dated May 4, 2017 in CN Application No. 2014101836665.
Office Action dated Jun. 9, 2017 in EP Application No. 14166596.8.
Office Action dated Jun. 9, 2017 in EP Application No. 14166591.9.
Office Action dated Mar. 30, 2018 in U.S. Appl. No. 14/850,450 by Gross.
Office Action dated Mar. 1, 2018 in EP Application No. 14166592.7.
Office Action dated Aug. 14, 2017 in CN Application No. 201410178318.9.
Office Action dated Sep. 28, 2017 in IN Application No. 2528/DELNP/2010.
Office Action dated Dec. 4, 2017 in CN Application No. 201410178374.2.
Office Action dated Nov. 13, 2017 in U.S. Appl. No. 14/193,692, by Gross.
Office Action dated May 18, 2018 in EP 14166591.9.

* cited by examiner

KEY FOR SECURING COMPONENTS OF A DRUG DELIVERY SYSTEM DURING ASSEMBLY AND/OR TRANSPORT AND METHODS OF USING SAME

CROSS-REFERENCE TO RELATED APPLICATIONS

This application is a Continuation-in-Part of U.S. patent application Ser. No. 12/244,666, filed on Oct. 2, 2008, which claims priority to U.S. Provisional Patent Application No. 60/997,459, filed Oct. 2, 2007, the disclosures of all of which are incorporated by reference herein.

This application is related to the U.S. Patent Application entitled DISENGAGEMENT RESISTANT TELESCOPING ASSEMBLY AND UNIDIRECTIONAL METHOD OF ASSEMBLY FOR SUCH, by the same applicants and filed on the same day, the disclosure of which is incorporated herein by reference.

BACKGROUND OF THE INVENTION

The present invention, in some embodiments thereof, relates to drug delivery systems and, more particularly, but not exclusively, to apparatuses and methods for securing components of a drug delivery system during assembly and/or transport.

Failure to use a delivery device or system, such as an insulin pen or auto-injector, correctly could result in a life or death emergency, or impact a patient's or caregiver's ability to manage a medical condition effectively. For the pharmaceutical manufacturer, such a failure could result in a massive backlash that may cause loss of market share, costly product recalls or worse.

The primary goal of any drug delivery system is to ensure that a patient receives a proper dose of a prescribed drug. In years past, if a device failed or was used incorrectly, patient or caregiver error was most often the culprit. While providing detailed instructions is important for any pharmaceutical manufacturer, failure to follow directions is no longer a viable excuse when a patient or caregiver is unable to operate a device or delivery system successfully.

Effective drug therapy and treatment typically involves more than simply having an effective molecule. Rather, it is the combination of a safe drug within a suitable container and/or delivery system.

Historically, pharmaceutical manufacturers have focused, and rightly so, on the efficacy and safety of the drug product. However, if the drug is to achieve its therapeutic objective, then its primary container and delivery system must be both compatible with the drug and stable over time, Today's injectable therapies can take many forms. Liquid drugs may use a traditional syringe and vial; a prefilled syringe; or a delivery system such as an auto-injector, pen device or patch injector. Lyophilized drug products (requiring reconstitution with water for injection) may use a kit containing a transfer device, syringe or needle, and containers of the drug and water.

The container format itself also should be considered. Vials may be used for initial use, but a syringe or cartridge system may provide the best solution for the patient when the system reaches the market. Once the primary container has been selected, efforts must be made to ensure that it works with the delivery system. Dimensional tolerances and functionality should be tested to ensure proper activation and gliding forces.

Recognizing how the patient or caregiver interacts with the delivery system is essential to ensuring success in the market. Even the most innovative drug can provide the appropriate therapeutic benefit to the patient only if it can be delivered effectively and the patient adheres to the treatment regimen. Patients or caregivers may choose one product over another based on dose frequency, pain associated with dosing, or ease of use or mobility of the delivery system. Simply put, packaging can differentiate a product's market acceptance.

One frequent ease of use issue that is encountered by users of drug delivery systems, for example patch injectors like the SmartDose® Electronic Patch Injector System offered by Medimop Medical Projects Ltd., a subsidiary of West Pharmaceutical Services, Inc., is movement of the operative parts during transport. For example, vibrations during transport may cause movements of screws causing a telescoping assembly (TSA) of the delivery system to extend. As result, when a cartridge containing the unintentionally extended telescoping assembly is inserted by the user, it may be difficult to close the door of the delivery system. Some users may interpret this as a malfunction and elect not use the unit.

International Patent Application Publication No. WO/2011/090956, the disclosure of which is incorporated herein by reference, describes a cartridge interface assembly characterized by a driving plunger including an outer shaft, and a driver including an inner shaft movable telescopically with respect to the outer shaft, wherein rotation of the driver causes the driving plunger to advance in a direction away from the driver. When the cartridge interface assembly is inserted in a cartridge in which a plunger is slidingly disposed, rotation of the driver causes the driving plunger to advance distally in the cartridge until abutting against the plunger. The shafts may tend to unscrew during transportation and handling before assembly, with the result that the position, which is the desirable position for assembly with the cartridge plunger, is not maintained. On the other hand, if the driver is tightened too much against the body of assembly in an effort to maintain the closed position of, this can increase the torque used by the motor to overcome the tight connection in order to start turning the driver, thereby overburdening the motor. To solve this double problem (possible opening of telescoping shafts or the driver being tightened too much), a locking assembly is provided

BRIEF SUMMARY OF THE INVENTION

An aspect of some embodiments of the invention relates to an assembly key used for securing a telescoping assembly of a drug delivery system during transport. In some embodiments of the invention, the drug delivery system is a patch injector.

In an exemplary embodiment of the invention, the assembly key is provided with a locking bit which is adapted to interface with at least one component of the telescoping assembly. In an embodiment of the invention, the locking bit is inserted into a key slot located on a pushing nut screw of the telescoping assembly. In some embodiments of the invention, the locking bit first passes through a bit aperture of a cartridge gear of the telescoping assembly, thereby linking the cartridge gear and pushing nut screw together, but also substantially or entirely preventing the turning of the telescoping assembly, for example as a result of vibrations during transport.

In some embodiments of the invention, the assembly key is removably attached to the cartridge gear. At least one clip is provided to the assembly key which snaps into at least one counterpart clip aperture located on the cartridge gear.

In some embodiments of the invention, the pushing nut screw is at least partially deformed in order to retain a mid screw located within the pushing nut screw. In an embodiment of the invention, retention of the mid screw substantially prevents rotation of the telescoping assembly, and thereby effectuates substantial stoppage of unintended extension of the telescoping assembly.

An aspect of some embodiments of the invention relates to a method for assembling a telescoping assembly and securing it for transport. In an embodiment of the invention, a mid screw of the telescoping assembly is threaded onto an internal screw of the telescoping assembly. A cartridge gear of the telescoping assembly is applied onto the internal screw from the same end of the internal screw that the mid screw was threaded, in an embodiment of the invention. In an embodiment of the invention, the three assembled components (the mid screw, the internal screw and the cartridge gear) are threaded into a pushing nut screw of the telescoping assembly, which is already attached to a pushing nut cover of the telescoping assembly.

In some embodiments of the invention, the three assembled components (the mid screw, the internal screw and the cartridge gear) are screwed into the pushing nut screw so that a bit aperture located on the cartridge gear is aligned with a key slot on the pushing nut screw.

An assembly key is installed onto the completed telescoping assembly by inserting a locking bit located on the assembly key into the bit aperture and further, into the key slot.

In some embodiments of the invention, at least one clip provided to the assembly key is inserted through at least one counterpart clip aperture located on the cartridge gear to removably attach the assembly key to the telescoping assembly.

In an embodiment of the invention, the locking bit inserted into the locking bit aperture and into the key slot substantially prevents rotation of the pushing nut screw and/or the unintended extension of telescoping assembly as a result of vibrations during transport.

In an embodiment of the invention, the assembly key is removed from the telescoping assembly after transport to enable normal operation of the telescoping assembly and the drug delivery system.

In an embodiment of the invention, the assembly key is economically manufactured and/or is constructed of inexpensive materials. Optionally, the assembly key is disposable and is disposed of after use.

An aspect of some embodiments of the invention relates to an alternative method for assembling a telescoping assembly and securing it for transport. In an embodiment of the invention, a pushing nut screw of the telescoping assembly is attached to a pushing nut cover of the telescoping assembly. A mid screw of the telescoping assembly is threaded into the pushing nut screw. In an embodiment of the invention, an internal screw is threaded into the mid screw. A cartridge gear of the telescoping assembly is installed at the end of the internal screw opposite the pushing nut cover.

In an embodiment of the invention, an assembly key is installed onto the completed telescoping assembly by inserting a locking bit of the assembly key into a bit aperture located on the cartridge gear and further, into a key slot of the pushing nut screw.

In some embodiments of the invention, at least one clip provided to the assembly key is inserted through at least one counterpart clip aperture located on the cartridge gear to removably attach the assembly key to the telescoping assembly.

In an embodiment of the invention, the locking bit inserted into the locking bit aperture and into the key slot substantially prevents rotation of the pushing nut screw and/or the unintended extension of telescoping assembly as a result of vibrations during transport.

In an embodiment of the invention, the assembly key is removed from the telescoping assembly after transport to enable normal operation of the telescoping assembly and the drug delivery system.

In an embodiment of the invention, the pushing nut screw is at least partially deformed near or at the end opposite the pushing nut cover to create a stop for the mid screw, creating an additional means for securing the telescoping assembly during transport. Optionally, the stop is created by driving a shot pin into the pushing nut screw 104, possibly heated or ultrasonic.

An aspect of some embodiments of the invention relates to a method for using an assembly key to secure a telescoping assembly of a drug delivery system. In an embodiment of the invention, the assembly key is removably attached to at least one component of the telescoping assembly by inserting a locking bit of the assembly key into a bit aperture of a cartridge gear of the telescoping assembly and further, into a key slot of a pushing nut screw of the telescoping assembly.

In some embodiments of the invention, at least one clip provided to the assembly key is inserted through at least one counterpart clip aperture located on the cartridge gear to removably attach the assembly key to the telescoping assembly.

In an embodiment of the invention, the locking bit inserted into the locking bit aperture and into the key slot substantially prevents rotation of the pushing nut screw and/or the unintended extension of telescoping assembly as a result of vibrations during transport.

In an embodiment of the invention, the assembly key is removed from the telescoping assembly after transport to enable normal operation of the telescoping assembly and the drug delivery system.

An aspect of some embodiments of the current invention relates to an assembly key that may secure a telescoping assembly in a desired configuration and/or assist assembly of the telescoping assembly into a medicine dispensing device. For example, a telescoping assembly may be delivered to a drug supplier for assembly into a syringe containing a drug. The drug supplier may need to orient the telescoping assembly and/or insert a portion of the assembly into a syringe and/or connect the telescoping assembly to a plunger inside the syringe. An assembly key may optionally have markings and/or a geometry to assist orientation of the telescoping assembly. The assembly key may optionally secure the telescoping assembly in the proper configuration for assembly to the syringe. The assembly key may optionally provide a gripping surface for attaching the telescoping assembly to the plunger of the syringe. Optionally, the plunger is considered to be a component of the telescoping assembly.

An aspect of some embodiments of the current invention relates to an assembly key that may secure a telescoping assembly in a desired configuration for deployment by an end user. An end user may optionally insert a cartridge into a drug delivery device (for example an infuser and/or a patch injector) and/or administer the drug. An assembly key may optionally include markings and/or a geometry to assist orientation of the telescoping assembly. The assembly key may optionally secure the telescoping assembly in the proper configuration for insertion into a delivery device and/or drug delivery. In some embodiments, the assembly key may be removed before the beginning of drug delivery. The assembly key may optionally include features that assist simple, intuitive removal of the key before use.

There is provided in accordance with an exemplary embodiment of the invention, a method of securing an assembly of a drug delivery system, comprising: configuring at least a first component and a second component of the assembly in a closed configuration ready for placement into the drug delivery system; installing an assembly key including a locking element on the assembly to secure the assembly in the configuration; and, transporting the assembly with the assembly key installed.

In an embodiment of the invention, the method further comprises employing the assembly key to facilitate assembly of the assembly during manufacture.

In an embodiment of the invention, the transporting is to an end user.

In an embodiment of the invention, the method further comprises removing the assembly key after transporting.

In an embodiment of the invention, the method further comprises disposing of the assembly key after removing.

In an embodiment of the invention, the removing is by the end user.

In an embodiment of the invention, the securing includes preventing relative movement of at least two components of the assembly.

In an embodiment of the invention, installing the assembly key includes inserting the locking element of the assembly key through a bit aperture of a first component of the assembly and into a slot, aligned with the bit aperture, of a second component of the assembly, thereby preventing relative movement of the first component and the second component.

In an embodiment of the invention, installing the assembly key includes inserting the locking element of the assembly key through a key aperture of a first component of the assembly and into a key slot, aligned with the key aperture, of a second component of the assembly, thereby preventing relative movement of the first component and the second component.

In an embodiment of the invention, installing comprises removably inserting at least one clip into a first component of the assembly.

In an embodiment of the invention, the at least one clip is installed through the top of the first component.

In an embodiment of the invention, the at least one clip is installed on the outside of the first component.

In an embodiment of the invention, a driver component is the first component and an actuating component is the second component.

In an embodiment of the invention, the driver component includes a gear.

In an embodiment of the invention, wherein the actuating component includes a pushing nut cover configured for pushing a plunger of a syringe.

In an embodiment of the invention, the method further comprises providing the assembly key with a distinguishing feature to make the assembly key easier to identify for removing.

In an embodiment of the invention, the method further comprises using the assembly key as a mechanical linkage between the assembly and an assembly machine during manufacture of the assembly key prior to transporting.

In an embodiment of the invention, the method further comprises using the assembly key to sense the orientation of the assembly during manufacturing.

In an embodiment of the invention, the method further comprises using the assembly key to screw the assembly into a plunger of the drug delivery system.

In an embodiment of the invention, installing includes passing a locking bit of the assembly key through a bit aperture in a first of the at least two components and into a key slot of a second of the at least two components.

There is provided in accordance with an exemplary embodiment of the invention, a system for preventing unintended linear extension of an assembly of a drug delivery system during transport, comprising: an assembly including at least a first component and a second component in a closed configuration; and, an assembly key including a locking element removably installed on the closed assembly, wherein the locking element of the assembly key prevents motion of at least the first component and the second component with respect to each other, thereby preventing extension of the closed assembly during transport.

In an embodiment of the invention, at least the first component and the second component are interconnected by a screw thread and wherein relative rotation of the first and second component causes extension of the assembly.

In an embodiment of the invention, the assembly key includes at least one locking element configured to interplay with at least the first component and the second component such that the two components are prevented from rotating with respect to each other, thereby preventing linear extension of the assembly.

In an embodiment of the invention, the first component of the assembly includes an actuating component for pushing a plunger of the drug delivery system.

In an embodiment of the invention, the first component is provided with a key slot adapted as a counterpart to the locking element.

In an embodiment of the invention, the second component includes a driver component.

In an embodiment of the invention, the second component includes a gear.

In an embodiment of the invention, the second component is provided with a key aperture adapted to the locking element therethrough.

In an embodiment of the invention, the key aperture on the second component aligns with a key slot on the first component to pass the locking element through the first and second components together.

In an embodiment of the invention, the assembly key further comprises at least one clip for removably attaching the assembly key to at least one component of the assembly.

In an embodiment of the invention, the system further comprises at least one clip aperture provided to the at least one component of the assembly configured as a counterpart to the at least one clip.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, are not to scale, and are for purposes of illustrative discussion of embodiments of the invention. In this regard, the description taken with the drawings makes apparent to those skilled in the art how embodiments of the invention may be practiced.

In the drawings.

DETAILED DESCRIPTION OF THE INVENTION

Figure 1:
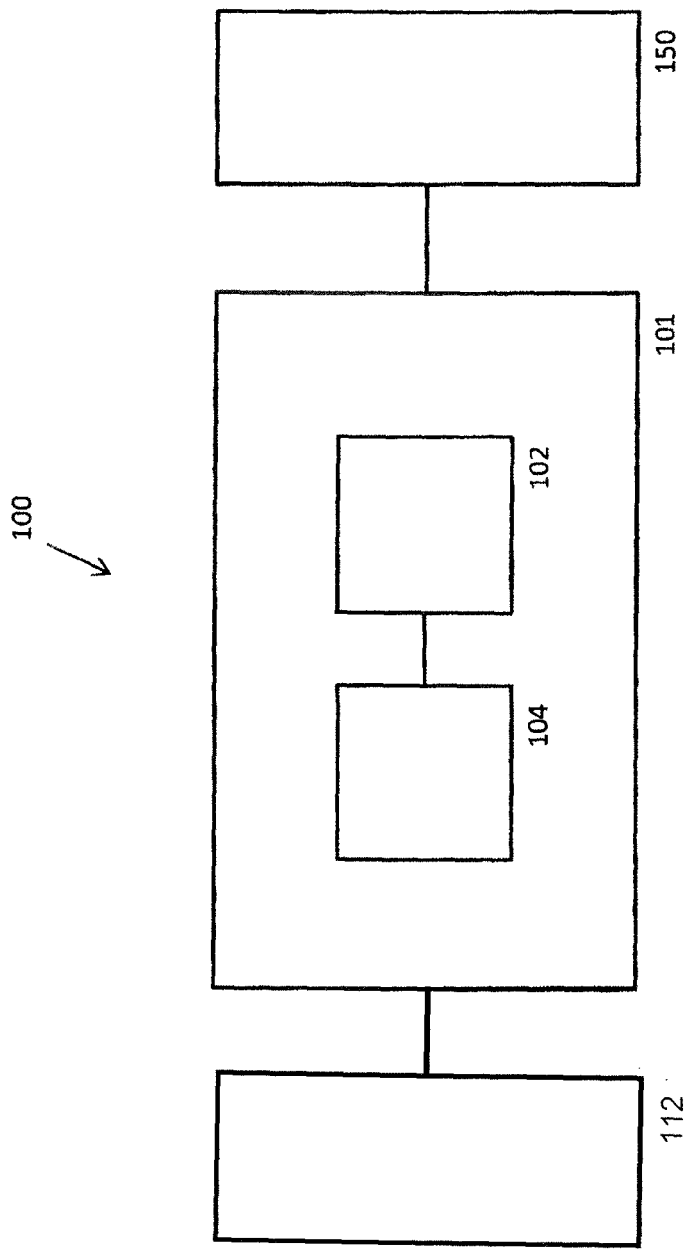
FIG. 1 is a block diagram illustrating a system for preventing unintended extension of a telescoping assembly of a drug delivery system, in accordance with an exemplary embodiment of the invention.

The present invention, in some embodiments thereof, relates to drug delivery systems and, more particularly, but not exclusively, to apparatuses and methods for securing components of a drug delivery system during transport.

Before explaining at least one embodiment of the invention in detail, it is to be understood that the invention is not necessarily limited in its application to the details of construction and the arrangement of the components and/or methods set forth in the following description and/or illustrated in the drawings and/or the exemplary embodiments. The invention is capable of other embodiments or of being practiced or carried out in various ways.

Referring now to the drawings, FIG. 1 is a block diagram illustrating a system 100 for preventing unintended movement of a telescoping assembly 101 of a drug delivery system, in accordance with an exemplary embodiment of the invention. In an embodiment of the invention, the system is comprised of the telescoping assembly 101, a plunger 112 advanced by the telescoping assembly 101, and an assembly key 150. In an embodiment of the invention, the assembly key 150 is a separate component from the assembly 101, provided with latches and/or clips to removably attach it to at least one component of the assembly and which substantially retains the assembly 101 in a set configuration by preventing the linear movement of at least a first component 102 of the telescoping assembly 101 with respect to at least a second component 104 of the assembly 101. In an embodiment of the invention, the set configuration is a closed configuration.

Figure 3:
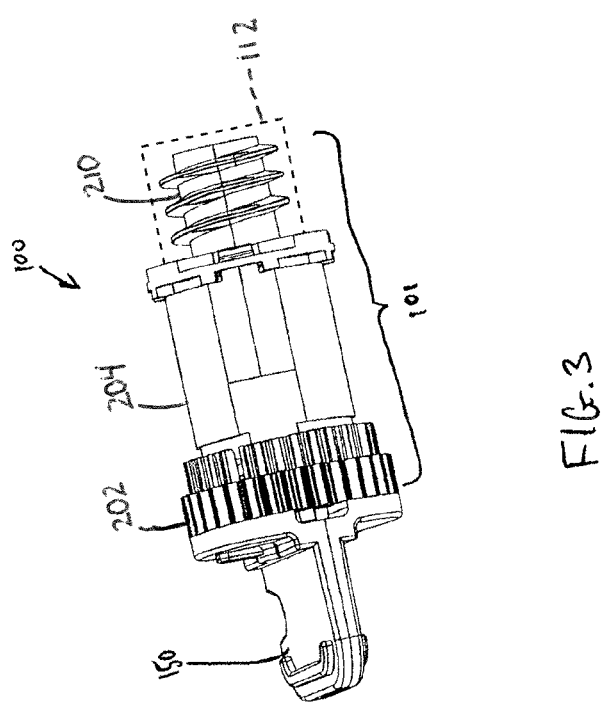
FIG. 3 is a perspective view of the telescoping assembly of a drug delivery system with an assembly key of FIG. 2 in a closed configuration, in accordance with an exemplary embodiment of the invention.
Figure 4:
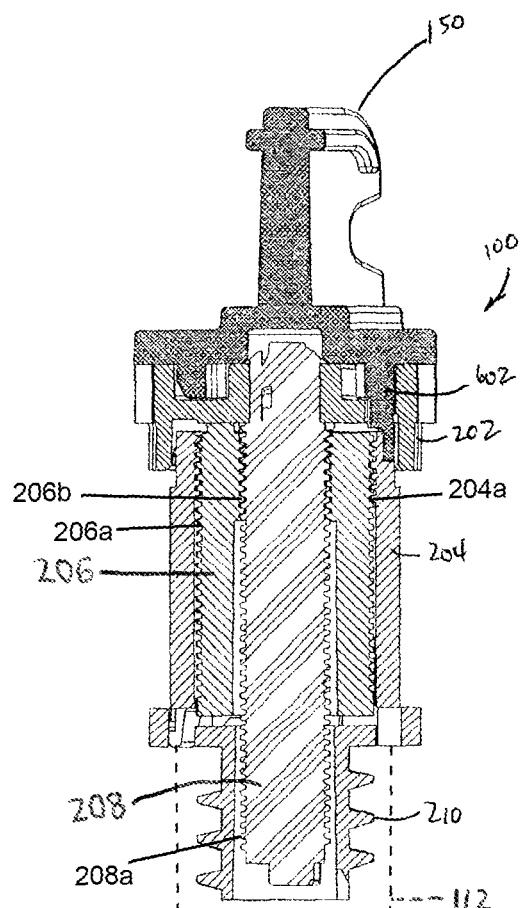
FIG. 4 is a perspective, cross-sectional view of the closed telescoping assembly with assembly key of FIG. 3, in accordance with an exemplary embodiment of the invention.

In some embodiments of the invention, extension of the telescoping assembly 101 is achieved by rotation of at least one of the components of the assembly 101. For example, the assembly key 150 substantially prevents rotation of the assembly 101 by interlocking at least two components of the assembly 101, which in some embodiments has at least four components, as shown in FIGS. 2-4, to prevent their rotation with respect to each other.

In some embodiments of the invention, the drug delivery system is a patch injector system. In some embodiments of the invention, the telescoping assembly 101 is an operative component of a cartridge of a patch injector system, wherein the disposable and/or interchangeable cartridge contains a pre-measured dose of a drug to be administered to a patient using the drug delivery system.

It should be understood that in order to utilize a smaller, more economical motor, the force used to screw the telescoping assembly 101 in order to extend and retract it may optionally be minimized with low friction threading. This low friction threading allows for easier movement using the motor, but it is also what allows for easy unintended movement of the assembly 101 as a result of vibrations, for example during transport.

Figure 2:
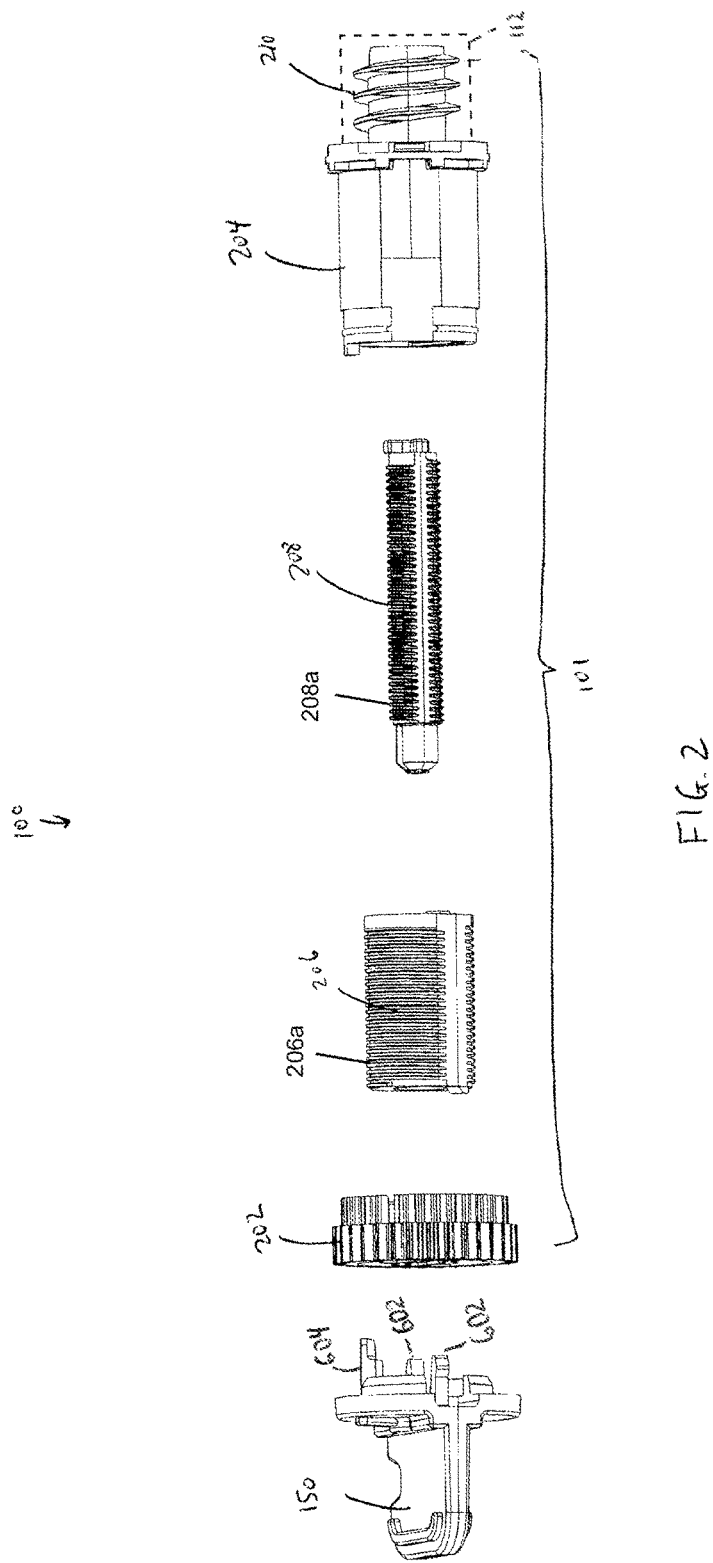
FIG. 2 is an exploded perspective view of a telescoping assembly of a drug delivery system, in accordance with an exemplary embodiment of the invention.

FIG. 2 illustrates an exploded perspective view of a telescoping assembly 101 of a drug delivery system, in accordance with an exemplary embodiment of the invention. In an embodiment of the invention, telescoping assembly 101 is comprised of at least one second component/driver component, for example a cartridge gear 202, and/or at least one first component—that is, at least one external screw, for example a pushing nut screw 204, and/or at least one mid screw 206, and/or an internal screw 208 and/or a actuating component, for example a pushing nut cover 210 (shown in FIG. 2 pre-attached to pushing nut screw 204) for pushing a syringe plunger 112, shown in phantom in FIGS. 2-4. Telescoping assembly 101 includes three elongated threaded elements (pushing nut screw 204, mid screw 206 and internal screw 208) which move longitudinally with respect to one another to telescope (extend or close) the assembly, in an embodiment of the invention. The elongated elements may be interconnected by screw threads which drive the longitudinal movement when the elongated elements are rotated relative to one another. Thus, as shown in FIGS. 2-4, each elongated threaded element (pushing nut screw 204, mid screw 206 and internal screw 208) is a component having screw threads: pushing nut screw 204 has internal screw threads 204a (FIG. 4); mid screw 206 has external screw threads 206a and internal screw threads 206b (FIGS. 2 and 4); and internal screw 208 has external screw threads 208a (FIG. 4). As shown in FIG. 4, pushing nut screw 204 is connected by screw threads 204a and 206a to mid screw 206, and internal screw 208 is interconnected by a screw threads 208a and 206b to mid screw 206, such that relative rotation of the first component of any two of the components with respect to a second component interconnected to the first component by a screw thread may cause extension of the telescoping assembly. Alternatively or additionally, a telescoping assembly may include two, four or more elongated elements that may move longitudinally with respect to each other and/or may be interconnected by screw threads and/or may be driven by relative rotation (for example, as shown in FIGS. 2-4, pushing nut screw 204, mid screw 206 and internal screw 208).

In an embodiment of the invention, an assembly key 150 is provided to the telescoping assembly 101 to secure the telescoping assembly 101 for transport and to optionally assist with assembly of the telescoping assembly 101 into a syringe and/or a plunger of the syringe. In some exemplary embodiments of the invention, the telescoping assembly 101 is configured to interplay with assembly key 150 to secure the telescoping assembly 101 for transport and/or assembly. For example, the telescoping assembly 101 is configured to be secured by inserting a locking element, for example, locking bit 602, shown and described in more detail with respect to FIGS. 6A-7B, of the assembly key 150 into at least one component of the telescoping assembly 101 thereby locking it to prevent unintended extension of the assembly 101, in an exemplary embodiment of the invention. In some embodiments of the invention, the at least one component of the assembly 101 into which the locking bit 602 is inserted is pushing nut screw 204.

In an embodiment of the invention, pushing nut cover 210 is attached to a plunger 112 (FIGS. 2-4) or stopper (not shown) in the cartridge of the patch injector. The plunger may provide a fluid proof seal against the liquid in the cartridge and which pushes the fluid out of the cartridge and into the patient when the telescoping assembly 101 extends and activates/instigates the pushing of the pushing nut cover 210.

In an embodiment of the invention, at least one component is manufactured from a medical grade polymer, for example Polybutylene Terephthalates (PBTs), Ticona Celanex 2402MT, Ticona Celanex 2405MT, Delrin 500AL and Delrin 500P. In some embodiments of the invention, at least one component is manufactured from a plurality of materials, for example the gears are Ticona Celanex 2402MT but the threads are Ticona Celanex 2405MT.

In an embodiment of the invention, the cartridge gear is approximately 12 mm in diameter. In some embodiments of the invention, the extension achieved by the telescoping assembly is approximately 11 mm (for example, the 11 mm is a total amount of extension of a plurality of individual components which extend and contribute to the total), although it should be understood that virtually any length of extension could be achieved by any number of components operatively connected to one another. In some embodiments of the invention, the assembly key diameter approximately matches that of the cartridge gear.

FIG. 3 is a perspective view of a telescoping assembly 101 with an assembly key 150 of a telescoping portion 101 of a drug delivery system 100 that is closed (in a closed configuration) and locked by assembly key 150, in a typical secured configuration for transport and/or assembly and/or use in accordance with an exemplary embodiment of the invention. The telescoping portion 101 is attachable to the plunger 112 (shown in phantom) via the pushing nut cover 210.

FIG. 4 is a perspective, cross-sectional view of the telescoping assembly 101 of FIG. 3 in a closed configuration, in accordance with an exemplary embodiment of the invention. In the example of FIG. 3, assembly key 150 is locked to cartridge gear 202 and/or locking bit 602 of the assembly key 150 is shown interfacing with the pushing nut screw 204 in a closed configuration. In an embodiment of the invention, assembly key prevents the turning of the pushing nut screw 204 with respect to cartridge gear 202, thereby preventing substantially or entirely the unintended extension of the telescoping assembly. A handle on the proximal end of assembly key 150 may provide a gripping point and/or locking bit 602 may provide a torque point for twisting pushing nut screw 204 and/or pushing nut cover 210 For example, nut cover 210 may be inserted into a syringe and assembly key 150 may be used to twist pushing nut cover 210, screwing it into the plunger 112 (shown in phantom).

Figure 5:
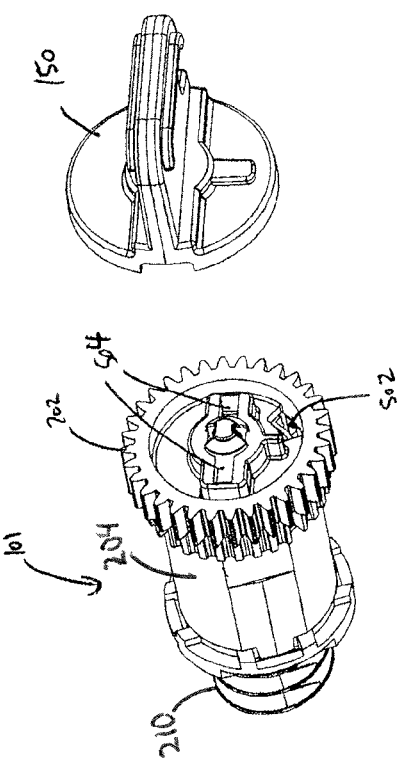
FIG. 5 is a perspective view of the closed telescoping assembly of FIG. 3 showing the top of the cartridge gear with the assembly key removed, in accordance with an exemplary embodiment of the invention.

FIG. 5 is a perspective view of the telescoping assembly 101 of FIG. 3 in a closed configuration showing the top of the cartridge gear 202 with the assembly key 150 removed, in accordance with an exemplary embodiment of the invention. In some embodiments of the invention, in the closed configuration shown, locking bit 602 is inserted through a bit aperture 502 in the cartridge gear 202 before it engages with a slot in the pushing nut screw 204. The assembly key 150 is provided with at least one clip 604, shown and described in more detail in FIGS. 6A-6C, which is removably attached to telescoping assembly 101 by inserting the at least one clip 604 through at least one counterpart clip aperture 504 located on the cartridge gear 202, in some embodiments of the invention. Additionally or alternatively, clip 604 may serve as a locking element, for example locking assembly key 150 to cartridge gear 202 and/or pushing nut screw 204. Additional details are shown in FIG. 4, wherein the at least one clip 604 is shown passing through a clip aperture 504 and through cartridge gear 202, in an embodiment of the invention.

Figure 6A:
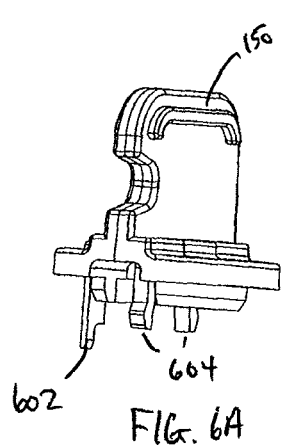
FIGS. 6A-6C are perspective views of the assembly key, in accordance with an exemplary embodiment of the invention.
Figure 6B:
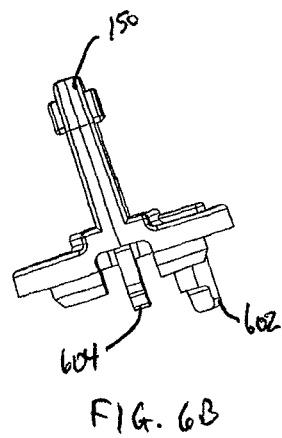
Figure 6C:
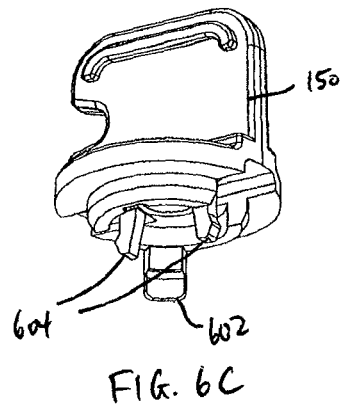

FIGS. 6A-6C are perspective views of the assembly key 150, in accordance with an exemplary embodiment of the invention. Shown in more detail in the various views are the locking bit 602 and the at least one clip 604.

Figure 7B:
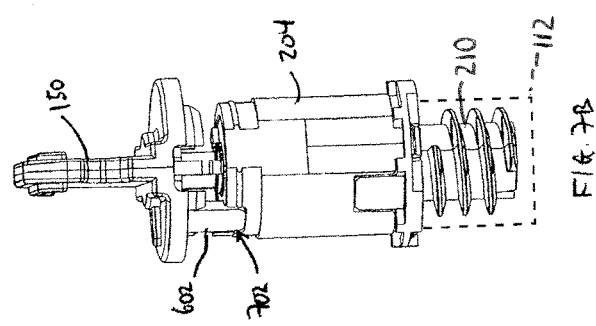
FIG. 7B is a close-up, perspective view of the assembly key engaged with the key slot, in accordance with an exemplary embodiment of the invention.
Figure 7A:
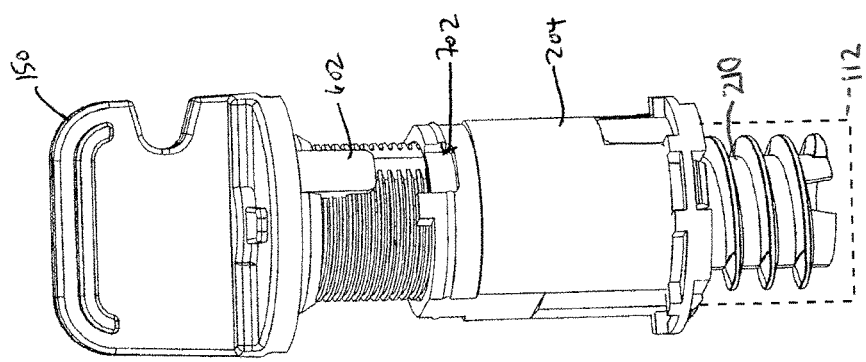
FIG. 7A is a perspective view of a telescoping assembly showing a key slot in a component of the assembly which acts as a counterpart to the assembly key, in accordance with an exemplary embodiment of the invention.

FIG. 7A is a perspective view of a telescoping assembly 101 showing a key slot 702 in a component of the assembly 101 which acts as a counterpart to the assembly key 150, in accordance with an exemplary embodiment of the invention. In some embodiments of the invention, the key slot 702 is located on the assembly key 150 key side of the pushing nut screw 204. In some embodiments of the invention, the key slot 702 aligns with the bit aperture 502 of the cartridge gear 202 (not shown in FIGS. 7A-7B, but shown in FIG. 5) whereby the locking bit 602 can be inserted through the bit aperture 502 and into the key slot 702.

FIG. 7B is a close-up, perspective view of the locking bit 602 of the assembly key 150 engaged with the key slot 702, in accordance with an exemplary embodiment of the invention. FIG. 7B does not show the cartridge gear 202 to make this configuration more visible, which in an embodiment of the invention would nominally surround the viewable portion of the pushing nut screw 204 and locking bit 602 in this Figure.

Figure 8:
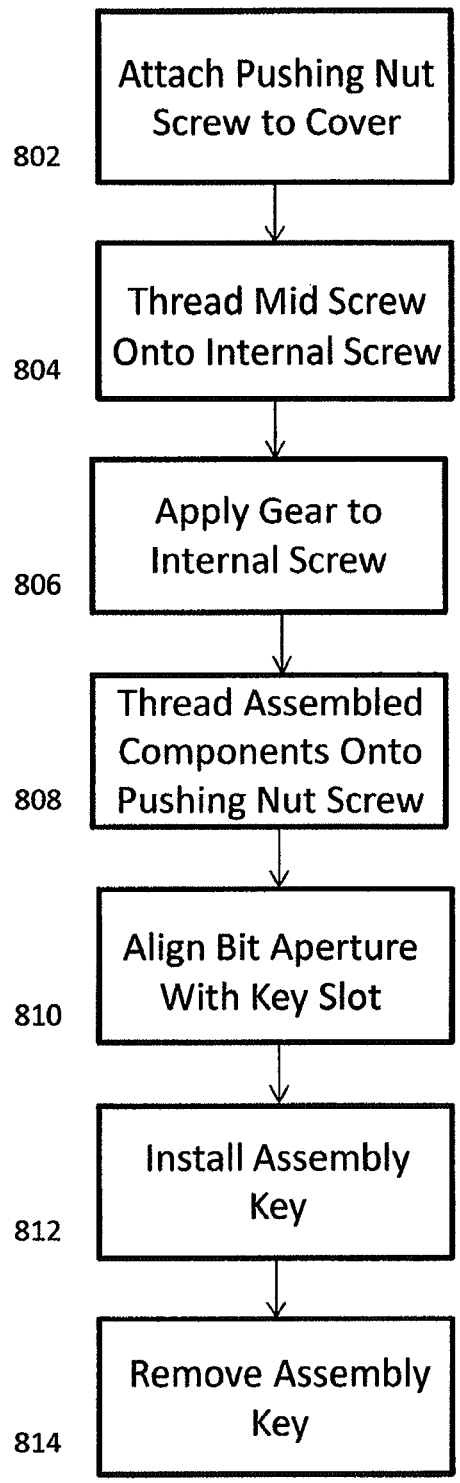
FIG. 8 is a flowchart of a method for assembling a telescoping assembly of a drug delivery system while also securing it for transport, in accordance with an exemplary embodiment of the invention.

FIG. 8 is a flowchart of a method for configuring a telescoping assembly 101 of a drug delivery system and/or securing it for assembly and/or transport and/or deployment, in accordance with an exemplary embodiment of the invention. In an embodiment of the invention, the mid screw 206 is threaded (804) onto the internal screw 208 so that the threads on the exterior circumference of the mid screw are positioned substantially towards the pushing nut screw cover 210. The cartridge gear 202 is applied (806) onto the internal screw 208 at the end opposite the pushing nut cover 210, in an embodiment of the invention. In an embodiment of the invention, the three components 202, 206, 208 are threaded (808) into the pushing nut screw 204 by engaging the threads on the exterior circumference of the mid screw 206 with threads located on the inner circumference of the pushing nut screw 204, which is already attached (802) to the pushing nut cover 210. In an embodiment of the invention, the three components are screwed into the pushing nut screw 204 so that the bit aperture 502 located on the cartridge gear 202 is aligned (810) with the key slot 702 on the pushing nut screw 204.

The assembly key 150 is installed (812) onto the telescoping assembly 101 by inserting the locking bit 602 into the bit aperture 502 and further, into the key slot 702. Additionally and concurrently, the at least one clip 604 is inserted through the at least one counterpart clip aperture 504 located on the cartridge gear 202 to removably attach the assembly key 150 to the telescoping assembly 101. In an embodiment of the invention, the locking bit 602 inserted into the locking bit aperture 502 and into the key slot 702 substantially prevents rotation of the pushing nut screw 204 with respect to the cartridge gear 202. Assembly key 150 may optionally supply a way of aligning and/or gripping pushing nut screw 204 and/or cartridge gear 202, Assembly key 150 may optionally prevent the unintended extension and/or closing of telescoping assembly 101.

In an embodiment of the invention, the assembly key 150 is removed (814) from the telescoping assembly 101 after transport to enable normal operation of the telescoping assembly 101 and the drug delivery system. Removal (814) of assembly key 150 may be by simple pulling away from the telescoping assembly. Simple removal (814) of assembly key may contribute to the ease of use of the device.

Figure 9:
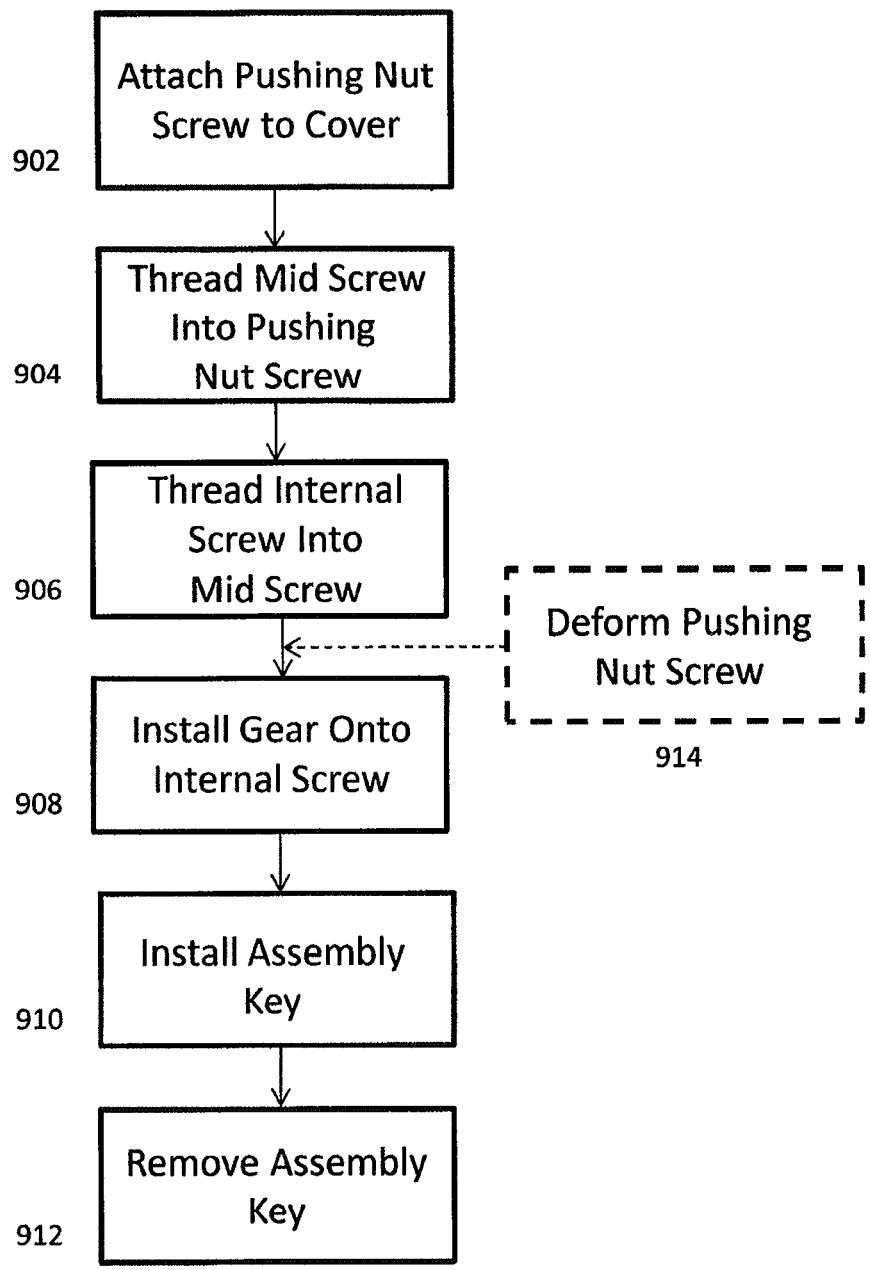
FIG. 9 is a flowchart of an alternative method for assembling a telescoping assembly of a drug delivery system while also securing it for transport, in accordance with an exemplary embodiment of the invention.

FIG. 9 is a flowchart of an alternative method for configuring a telescoping assembly 101 of a drug delivery system while also securing it for transport, in accordance with an exemplary embodiment of the invention. In an embodiment of the invention, pushing nut screw 204 is attached (902) to the pushing nut cover 210. The mid screw 206 is threaded (904) into the pushing nut screw 204 by engaging the threads on the exterior circumference of the mid screw 206 with threads on the interior circumference of the pushing nut screw 204. In an embodiment of the invention, the internal screw 208 is threaded (906) into the mid screw 206. The internal screw 208 is optionally over rotated to make installation of the cartridge gear 202 easier. In an embodiment of the invention, the cartridge gear 202 is installed (908) onto the inner screw aligning the bit aperture 502 of the cartridge gear 202 with the key slot 702 of the pushing nut screw 204 and, if the inner screw 208 was over rotated, the inner screw 208 is returned to a stop position.

In some embodiments of the invention, the pushing nut screw 204 is at least partially deformed (914) near or at the end opposite the pushing nut cover 210 to create (912) a stop for the mid screw 206. Optionally, the stop is created by driving a shot pin into the pushing nut screw 204, possibly heated or ultrasonic.

Figure 10:
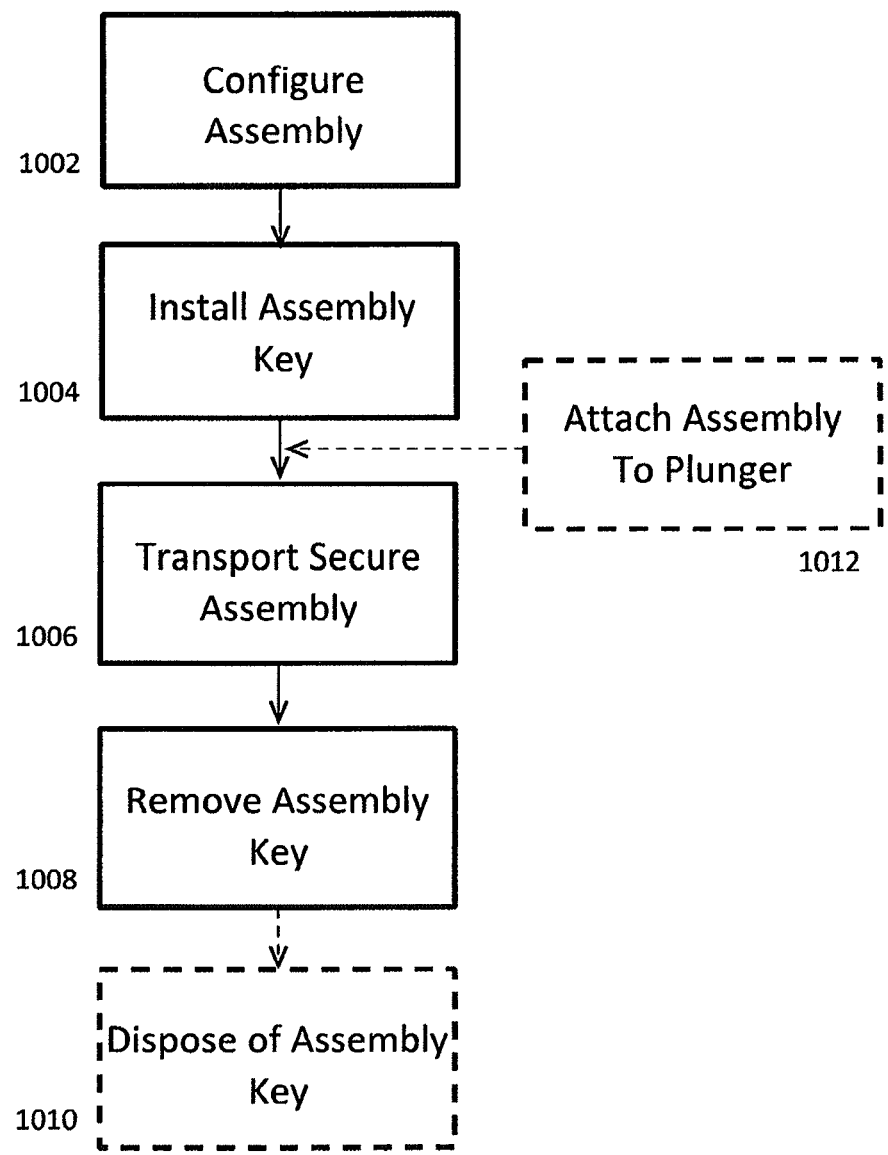
FIG. 10 is a flowchart of a method for using an assembly key to secure a telescoping assembly of a drug delivery system, in accordance with an exemplary embodiment of the invention.

FIG. 10 is a flowchart illustration of a method for assembling and using a drug delivery system, in accordance with an exemplary embodiment of the invention. In an embodiment of the invention, the telescoping assembly is configured (1002) for use, for example as described in FIGS. 8 and/or 9. In an embodiment of the invention, the assembly key 150 is installed (1004) on the telescoping assembly 101, securing the assembly 101. For example, securing may include removably attaching the assembly key 150 to at least one component of the telescoping assembly 101. The telescoping assembly is now secured, preventing unintended extension, for assembly and/or transport and/or deployment.

In some embodiments, after telescoping assembly 101 is configured (1002) and secured (1004), it may be placed into a drug delivery system. Optionally, assembly key 150 assists attachment (1012) of the telescoping assembly 150 into the syringe. For example, pushing nut cover 210 may be attached to a plunger of a syringe. Assembly key, supply a convenient gripping point and/or alignment indication for a person and/or a machine to hold pushing nut cover 210 and/or to insert it into the syringe and/or to align threads of pushing nut cover 210 to threads in the plunger and/or to twist pushing nut cover 210 to screw it into the plunger.

In some embodiments, the syringe and/or the telescoping assembly 101 may be transported (1006) to the end user. The assembly key 150 may optionally be left on the telescoping assembly 101 during transport (1006). For example, the telescoping assembly 150 may prevent the telescoping assembly from moving out of its proper configuration for example due to vibrations during transport (1006).

In some embodiments, once the syringe and/or the telescoping assembly 101 reach the end user, the assembly key may be removed (1008) and/or the syringe and/or the telescoping assembly 101 may be deployed. For example deployment may include inserting the syringe and/or assembly 101 into a delivery device (for example a patch injector). Transporting (1006) the telescoping assembly 101 with the assembly key 150 may help prevent the telescoping assembly 101 from extending during transport (1006). Unwanted extension of the telescoping assembly beyond its closed configuration might, for example, make it difficult to fit the assembly 101 and/or the syringe/cartridge into the injector.

The delivery device may optionally restrain the syringe and/or the plunger and/or pushing nut cover 210 from rotating while rotating cartridge gear 202 causing the telescoping assembly 101 to extend, pushing the plunger into the syringe and/or delivering the drug. In some cases, transporting (1006) telescoping assembly 101 with the assembly key 150 attached (1004) may prevent telescoping assembly 101 from closing up too much during transport. Over closing of the telescoping assembly 101 may for example cause thread lock within the telescoping assembly 101 which could cause failure of the delivery system.

In an embodiment of the invention, the assembly key 150 and/or the entire drug delivery system is disposed of (1010). For example, the delivery key 150 and/or the telescoping assembly and/or the delivery device may be made of safe materials that may be disposed of (1010) in municipal garbage.

With respect to the assemblies and methods described herein it should be understood that in an exemplary embodiment of the invention, the assembly 101, which is secured for transport as described herein, remains in a closed configuration and does not unintentionally linearly extend as a result of vibrations during transport. In an embodiment of the invention, "transport" is to be understood as moving from the manufacturer, through the distribution chain, and ultimately to the consumer. In some embodiments, "transport" is a sub-set of the chain described above. For example, as applied to transport on a truck from a port of entry to a distribution center. In an embodiment of the invention, such as any of those described herein, the assembly key provides sufficient locking force to ensure compliance under the ASTM D4169 performance testing of shipping containers and systems standards for combined air and rail transport. In some embodiments of the invention, the assembly key prevents unintended linear extension of the assembly while being subjected to extended vibrations up to 300 Hz. Optionally, extended vibration time is for hours, days or even weeks, for example in the case of cargo shipping overseas. In some embodiments of the invention, the assembly key prevents unintended linear extension of the assembly while being subjected to shocks up to 300 m/s2.

The secured assembly 101 is placed into a drug delivery system, for example a patch injector like the SmartDose® Electronic Patch Injector System offered by Medimop Medical Projects Ltd., a subsidiary of West Pharmaceutical Services, Inc. after the removal of the assembly key 150, in accordance with an exemplary embodiment of the invention.

Figure 11A:
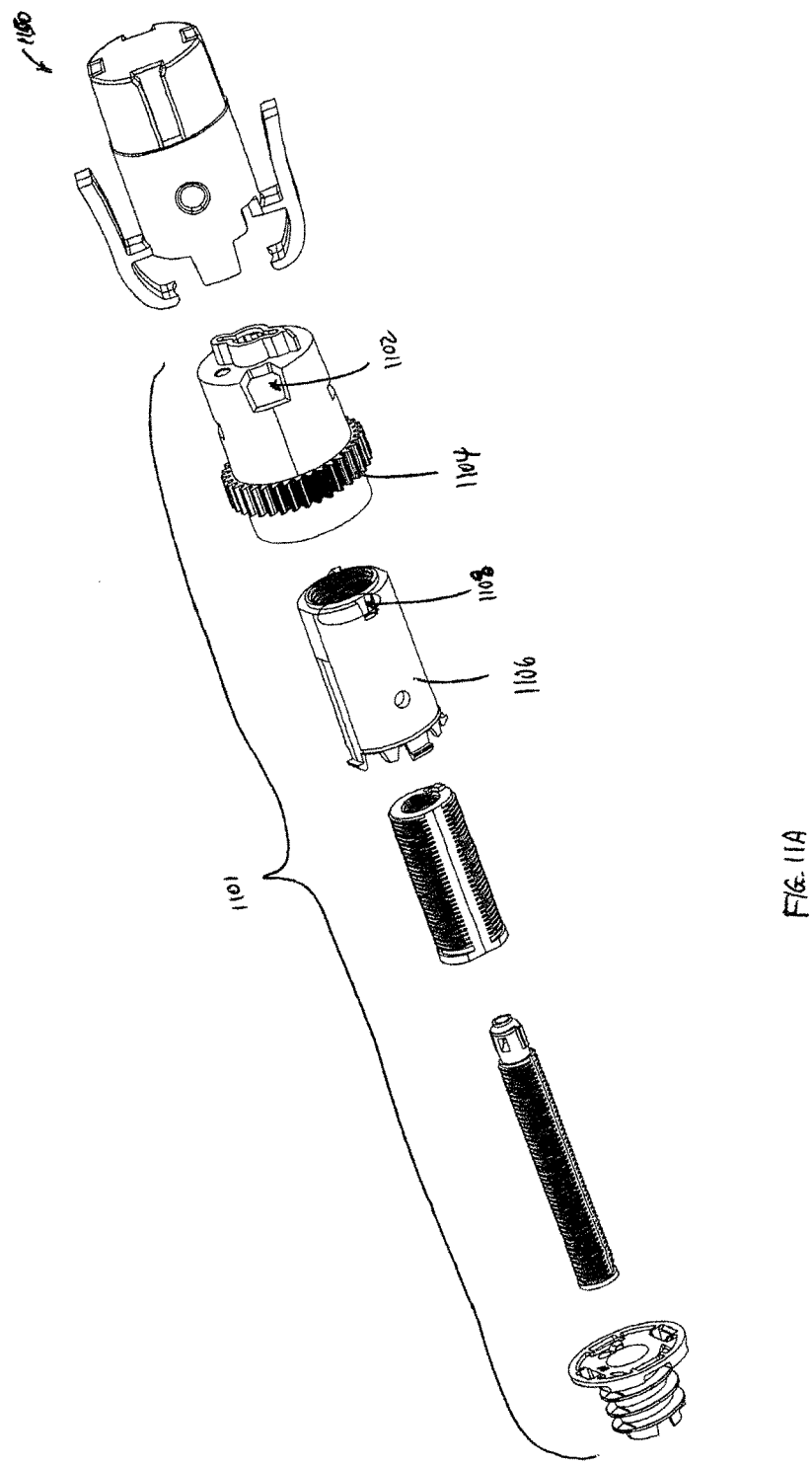
FIG. 11A is a perspective view of an alternative telescoping assembly showing a key slot in a component of the assembly which acts as a counterpart to an alternative assembly key, in accordance with an exemplary embodiment of the invention.

FIG. 11A is a perspective view of an alternative telescoping assembly 1101 showing at least one bit aperture 1102 in at least one component of the assembly which acts as a counterpart to at least one locking bit 1152 of an assembly key 1150, in accordance with an exemplary embodiment of the invention. In some embodiments of the invention, the bit aperture 1102 is located on the assembly key 150 key side of the cartridge gear 1104.

Figure 11B:
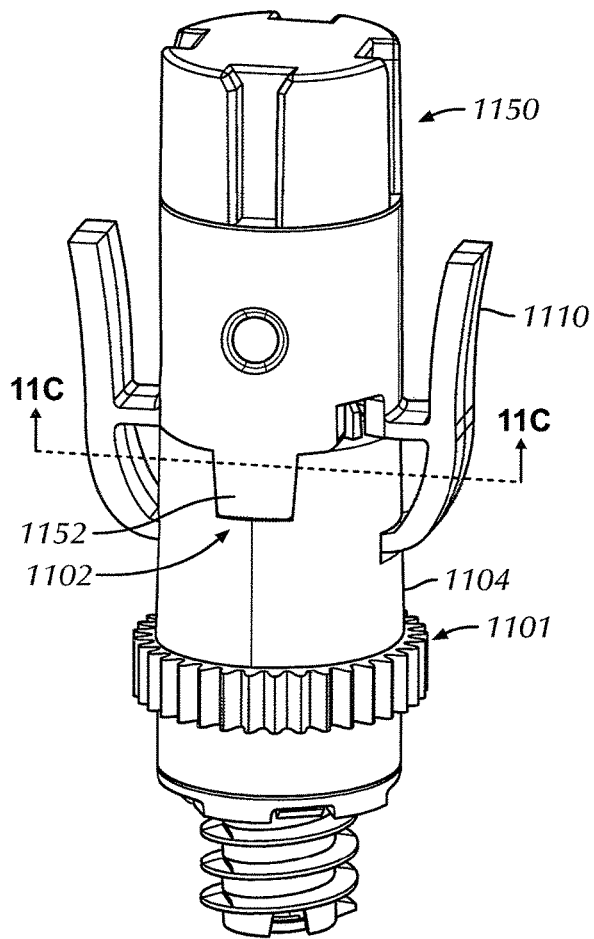
FIG. 11B is a perspective view of the assembled, closed alternative telescoping assembly of FIG. 11A, in accordance with an exemplary embodiment of the invention.

FIG. 11B is a perspective view of the assembled, closed alternative telescoping assembly 1101 of FIG. 11A, in accordance with an exemplary embodiment of the invention.

Figure 11C:
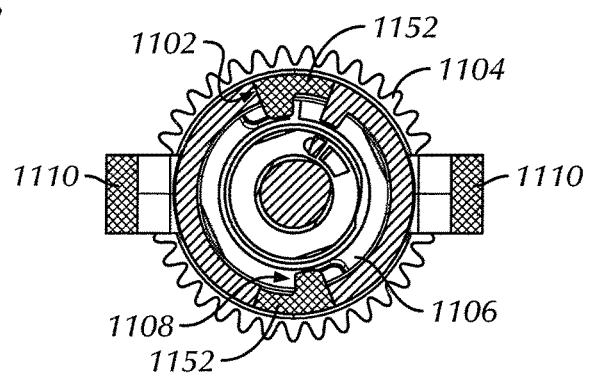
FIG. 11C is a cross-sectional view of the alternative telescoping assembly with assembly key of FIG. 11B, in accordance with an exemplary embodiment of the invention; and, FIGS. 12A-12C are perspective views of the alternative assembly key, in accordance with an exemplary embodiment of the invention.

FIG. 11C is a cross-sectional view of the alternative telescoping assembly 1101 with assembly key 1150 of FIG. 11B, in accordance with an exemplary embodiment of the invention.

In some embodiments of the invention, the bit aperture 1102 of the cartridge gear 1104 aligns with a key slot 1108 of the pushing nut screw 1106, enabling the locking bit 1152 of the assembly key 1150 to be inserted through the bit aperture 1102 and into the key slot 1108 preventing movement of the cartridge gear 1104 relative to the pushing nut screw 1106. In an embodiment of the invention, prevention of movement between the cartridge gear 1104 relative to the pushing nut screw 1106 prevents rotation of the assembly 1101, thereby preventing unintended extension of the assembly 1101.

In an embodiment of the invention, assembly key 1150 has a pair of clips 1110 for removal of the assembly key 1150 from the telescoping assembly 1101. In an embodiment of the invention, the pair of clips 1110 are squeezed sufficiently to cause deformation of the assembly key 1150 and to release the assembly key 1150 from the bit aperture 1102 and the key slot 1108. The use of deformable clips 1110 may make removal of assembly key 1150 easier for a nervous end user who may be reluctant to use force to remove assembly key 150 and/or who may become nervous that he might have broken the telescoping assembly 101 when he feels a snap giving way upon removal of assembly key 150. In some embodiments, deformation is elastic. In some embodiments, deformation is plastic. In some embodiments, deformation is a combination of elastic and plastic.

Figure 12A:
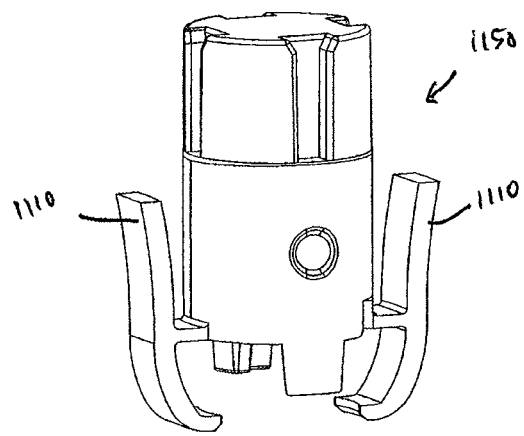
Figure 12B:
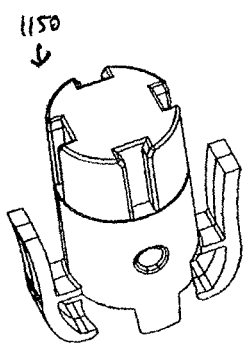
Figure 12C:
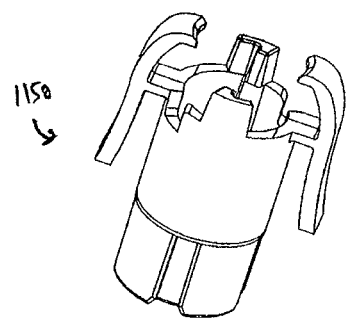

FIGS. 12A-12C are perspective views of the alternative assembly key 1150, in accordance with an exemplary embodiment of the invention.

In an embodiment of the invention, the assembly key 150, 1150 uses the same interface to attach to the telescoping assembly 101, 1101 as an assembly machine used for assembling the components of the telescoping assembly 101, 1101. In some embodiments of the invention, assembly key 150, 1150 is used as a linkage between the assembly machine and the telescoping assembly 101, 1101 during manufacturing. In an embodiment of the invention, after the telescoping assembly 101, 1101 is assembled, it is attached to a plunger of the drug delivery system, optionally by screwing. In an embodiment of the invention, the assembly key 150, 1150 provides a handle for manual or automatic screwing of the pushing nut cover into the plunger without extending, collapsing, screwing and/or unscrewing the telescoping assembly 150, 1150.

In an embodiment of the invention, the assembly key 150, 1150, used as a link between the telescoping assembly and the assembly machine during manufacturing, helps the assembly machine recognize the orientation of the telescoping assembly 101, 1101 during assembly, which can be important for proper assembly of the telescoping assembly 101, 1101 and insertion of it into the plunger. In an embodiment of the invention, mechanical sensing of the telescoping assembly's orientation using the assembly key obviates the need for more expensive optical sensing equipment.

In some embodiments of the invention, assembly keys as described herein are provided with a distinguishing feature, for example color, for easy identification by the customer for easier removal and/or disposal.

It is expected that during the life of a patent maturing from this application many relevant securing technologies will be developed and the scope of the terms securing is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for preventing unintended linear extension of a telescoping portion of a drug delivery system, the system for preventing unintended linear extension comprising:
   a telescoping assembly having a closed configuration and an extended configuration and an axis of linear telescoping movement, the telescoping assembly including at least a pushing nut screw and an internal screw in the closed configuration, the pushing nut screw and the internal screw being threadedly interconnected such that relative rotation between said pushing nut screw and said internal screw causes linear extension of said telescoping assembly to push fluid out of a cartridge injector, the pushing nut screw including a screw thread and the internal screw having a driver component applied thereto for rotating the internal screw; and,
   an assembly key including a locking element removably installed on the telescoping assembly in the closed configuration,
   wherein the locking element of the assembly key, when the assembly key is installed on the telescoping assembly with the pushing nut screw and the internal screw threadedly interconnected, prevents relative rotation and linear telescoping movement of at least the pushing nut screw and the internal screw with respect to each other in the closed configuration, thereby preventing linear extension of the telescoping assembly in the closed configuration.

2. The system according to claim 1, wherein the locking element of the assembly key extends parallel to the axis of linear telescoping movement to interact with at least the pushing nut screw and the internal screw such that the pushing nut screw and the internal screw are prevented from rotating with respect to each other in the closed configuration, and preventing such rotation thereby prevents the linear extension of said telescoping assembly.

3. The system according to claim 1, wherein the telescoping assembly includes an actuating component for pushing a plunger of a drug delivery system.

4. The system according to claim 3, wherein the pushing nut screw is provided with a key slot adapted as a counterpart to the locking element.

5. The system according to claim 1, wherein the driver component includes a gear.

6. The system according to claim 5, wherein the gear comprises a cartridge gear.

7. The system according to claim 1, wherein the internal screw is provided with a key aperture therethrough adapted to the locking element.

8. The system according to claim 7, wherein the telescoping assembly further comprises a mid screw threadedly connected to the internal screw and the pushing nut screw.

9. The system of claim 8, wherein the assembly key interplays with a key slot of the pushing nut screw.

10. The system according to claim 1, wherein a key aperture on the driver component aligns with a key slot on the pushing nut screw to pass the locking element through the pushing nut screw and the driver component together.

11. The system according to claim 1, wherein the assembly key further comprises at least one clip for removably attaching the assembly key to at least one of the pushing nut screw, the internal screw, and a third component of the telescoping assembly.

12. The system according to claim 11, further comprising at least one clip aperture configured as a counterpart to the at least one clip provided to at least one of the pushing nut screw, the internal screw, the third component, and a fourth component of the telescoping assembly.

13. A motor-driven drug delivery system, the system comprising:
   a motor;
   a telescoping assembly having a closed configuration and an extended configuration and an axis of linear telescoping movement, the telescoping assembly including a pushing nut screw and an internal screw in the closed configuration, the pushing nut screw and the internal screw being threadedly interconnected such that relative rotation between the pushing nut screw and the internal screw causes linear extension of the telescoping assembly to push fluid out of a cartridge injector, the pushing nut screw including a screw thread and the internal screw having a driver component applied thereto, the driver component being driven by the motor for rotating the internal screw; and
   an assembly key including a locking element removably installed on the telescoping assembly in the closed configuration, wherein the locking element of the assembly key, when the assembly key is installed on the telescoping assembly with the pushing nut screw and the internal screw threadedly interconnected, prevents relative rotation of the pushing nut screw and the internal screw with respect to each other in the closed configuration, thereby preventing linear extension of the telescoping assembly in the closed configuration.

14. The system according to claim 13, wherein the driver component comprises a gear.

15. The system according to claim 14, wherein the telescoping assembly further comprises a mid screw threadedly connected to the internal screw and the pushing nut screw.

16. The system according to claim 14, wherein the gear comprises a cartridge gear.

17. The system according to claim 13, wherein the locking element of the assembly key extends parallel to the axis of linear telescoping movement to interact with at least the pushing nut screw and the internal screw such that the pushing nut screw and the internal screw are prevented from rotating with respect to each other in the closed configuration, and preventing such rotation thereby prevents linear extension of the telescoping assembly.

18. The system according to claim 13, wherein the telescoping assembly includes an actuating component for pushing a plunger of the drug delivery system.

19. The system according to claim 18, wherein the pushing nut screw is provided with a key slot adapted as a counterpart to the locking element.

20. The system according to claim 13, wherein the internal screw is provided with a key aperture therethrough adapted to the locking element.

21. The system according to claim 13, wherein a key aperture on the driver component aligns with a key slot on the pushing nut screw to pass the locking element through the pushing nut screw and the driver component together.

22. The system according to claim 13, wherein the assembly key further comprises at least one clip for removably attaching the assembly key to at least one of the pushing nut screw, the internal screw, and a third component of the telescoping assembly.

23. The system according to claim 22, further comprising at least one clip aperture configured as a counterpart to the at least one clip provided to at least one of the pushing nut screw, the internal screw, the third component, and a fourth component of the telescoping assembly.

24. The system according to claim 23, wherein the telescoping assembly further comprises a mid screw threadedly connected to the internal screw and the pushing nut screw.

* * * * *